(12) United States Patent
Hirota et al.

(10) Patent No.: US 7,407,746 B2
(45) Date of Patent: Aug. 5, 2008

(54) BIOCHIP AND METHOD FOR PRODUCING THE SAME

(75) Inventors: Toshikazu Hirota, Nagoya (JP); Takao Ohnishi, Aichi-pref. (JP); Saichi Yamada, Ichinomiya (JP); Kazunari Yamada, Nagoya (JP); Yukihisa Takeuchi, Aichi-pref. (JP)

(73) Assignee: NGK Insulators, Ltd., Nagoya (JP)

( * ) Notice: Subject to any disclaimer, the term of this patent is extended or adjusted under 35 U.S.C. 154(b) by 401 days.

(21) Appl. No.: 10/068,292

(22) Filed: Feb. 6, 2002

(65) Prior Publication Data

US 2002/0155481 A1    Oct. 24, 2002

(30) Foreign Application Priority Data

Feb. 8, 2001    (JP)    ............... 2001-032829

(51) Int. Cl.
*C12Q 1/68*    (2006.01)
(52) U.S. Cl. ........................................................ 435/6
(58) Field of Classification Search .............. 435/4, 435/6, 7.1, 7.5, 7.8, 7.92–7.95, 287.1–287.3, 435/287.9, 289.9; 436/514, 518, 523, 520, 436/527, 532, 533; 427/212, 214, 220
See application file for complete search history.

(56) References Cited

U.S. PATENT DOCUMENTS

| | | | | |
|---|---|---|---|---|
| 4,308,799 A | * | 1/1982 | Kitagawa et al. | 101/457 |
| 4,681,870 A | * | 7/1987 | Balint et al. | 502/403 |
| 4,950,588 A | * | 8/1990 | Dattagupta | 435/6 |
| 5,183,735 A | * | 2/1993 | Lopez et al. | 435/6 |
| 5,474,796 A | * | 12/1995 | Brennan | 427/2.13 |
| 5,789,261 A | * | 8/1998 | Schwartz | 436/518 |
| 5,837,196 A | | 11/1998 | Pinkel et al. | |
| 5,851,840 A | * | 12/1998 | Sluka et al. | 436/525 |
| 5,856,203 A | * | 1/1999 | Robinson et al. | 436/518 |
| 6,255,051 B1 | * | 7/2001 | Hammond et al. | 435/6 |
| 6,350,618 B1 | * | 2/2002 | Borrelli et al. | 436/174 |
| 6,355,491 B1 | | 3/2002 | Zhou et al. | |
| 6,391,625 B1 | | 5/2002 | Park et al. | |
| 6,406,898 B1 | * | 6/2002 | Sakamoto et al. | 435/195 |
| 6,465,190 B1 | | 10/2002 | Hirota et al. | |
| 6,476,215 B1 | * | 11/2002 | Okamoto et al. | 536/25.3 |
| 6,576,419 B1 | * | 6/2003 | Wei et al. | 435/6 |
| 6,737,024 B1 | | 5/2004 | Eipel et al. | |
| 6,753,144 B1 | | 6/2004 | Hirota et al. | |
| 6,803,228 B1 | | 10/2004 | Caillat et al. | |
| 2002/0076832 A1 | * | 6/2002 | Pirrung et al. | 436/518 |
| 2002/0197454 A1 | | 12/2002 | Boussie et al. | |

FOREIGN PATENT DOCUMENTS

| | | |
|---|---|---|
| EP | 0 895 082 A2 | 2/1999 |
| EP | 0 895 083 A2 | 2/1999 |
| EP | 1 006 363 A2 | 6/2000 |
| EP | 1 026 259 A1 | 8/2000 |
| EP | 1 094 119 A2 | 10/2000 |
| EP | 1 143 252 A1 | 10/2001 |
| EP | 1 160 262 A1 | 12/2001 |
| JP | 6-40030 A | 2/1994 |
| JP | 10-15857 | 1/1998 |
| WO | 98/03257 | 1/1998 |
| WO | 99/04896 | 2/1999 |
| WO | 00/36145 | 6/2000 |
| WO | 00/54882 | 9/2000 |

OTHER PUBLICATIONS

Markus Beier and Jorg D. Hoheisel, "Versatile derivatisation of solid support media for covalent bonding on DNA-microchips", Nucleic Acid Research, 1999, vol. 27, No. 9, pp. 1970-1977.

* cited by examiner

*Primary Examiner*—Ann Y Lam
(74) *Attorney, Agent, or Firm*—Burr & Brown

(57) ABSTRACT

In a method for producing a biochip comprising a large number of spots based on captures, the spots are arranged on a base plate 10 by supplying, onto the base plate 10, a plurality of types of the captures to be used to specifically react with a specimen in order to obtain information on a structure or a function of the specimen, an immobilization-reinforcing solution 16 is supplied onto the base plate 10 (first supply step). Subsequently, a sample 14, which is obtained in a sample preparation step, is supplied onto the immobilization-reinforcing solution 16 having been supplied onto the base plate 10 to produce the biochip thereby (second supply step).

34 Claims, 16 Drawing Sheets

BIOCHIP AND METHOD FOR PRODUCING THE SAME

This application claims the benefit of Japanese Application 2001-032829, filed Feb. 8, 2001, the entirety of which is incorporated herein by reference.

BACKGROUND OF THE INVENTION

1. Field of the Invention

The present invention relates to a DNA microarray (DNA chip) which specifically reacts with a biochemical specimen and which is used for inspection equipment represented, for example, by a biochip to be used in order to obtain information on the structure and the function of the specimen. The biochip preferably has several hundreds to several ten thousands kinds of captures, especially DNA fragments or the like, for capturing the specimen, and the captures are aligned and fixed at a high density as minute spots on a base plate such as a microscopic slide glass. The present invention also relates to a method for producing the same.

2. Description of the Related Art

The methods for analyzing gene structures have remarkably progressed in recent years. A large number of gene structures represented by those of a human gene have been identified. The analysis of the gene structure as described above uses a DNA microarray (DNA chip) in which several hundreds to several ten thousands kinds of DNA fragments or the like are aligned and fixed as minute spots on a base plate such as a microscopic slide glass.

The methods widely used for forming the minute spots for the production of the DNA microarray are generally based on a system such as the QUILL system, the pin & ring system, and the spring pin system in which a sample solution is stamped onto the base plate by using a pin.

Even when any one of the foregoing methods is adopted, it is important to minimize the dispersion of the volume and the shape of each of the minute spots so that the distance between the respective minute spots is maintained to be constant. Further, it is necessary that the capture (corresponding to the DNA fragment or the like in the case of the DNA microarray), which specifically reacts with a specimen in the minute spot formed on the base plate and which is used to obtain information on the structure and the function of the specimen, is reliably immobilized on the base plate.

On the other hand, in order to realize a higher density, it is also greatly expected to develop a new method which is excellent in productivity and in which the shape control performance for the minute spot is satisfactory.

In the conventional production of the biochip, when the sample containing DNA fragments or the like is dropped onto the base plate to form minute spots, or when the chip is dealt with or treated thereafter, the minute spots may be peeled off. When the DNA fragments or the like are immobilized on the base plate in the DNA microarray, several techniques are adopted, in which a functional group is affixed to the DNA fragments themselves to facilitate immobilization, or the surface of the base plate is coated with a functional group layer. However, even when such a technique is adopted, the adopted technique is insufficient to avoid the peeling off of the minute spots.

Further, a technique is also adopted, in which a hydrophilic polymer or the like is dissolved in a sample containing DNA fragments or the like to reinforce the immobilization of the DNA fragment or the like onto the base plate. However, the cost may be increased, because it is necessary to mix the sample and an immobilization-reinforcing solution, and it is also necessary to use a large amount of the immobilization-reinforcing solution. Further, when such an immobilization-reinforcing solution and samples are previously mixed and supplied onto the base plate, it is necessary to consider the compatibility and the conformability between the immobilization-reinforcing solution and the thousands of potential samples. Therefore, the selection of the material for the immobilization-reinforcing solution has been restricted.

Further, the sample containing the immobilization-reinforcing solution has to be supplied onto the base plate in accordance with the conventional method. Therefore, a drawback arises in that only an immobilization-reinforcing solution, which has physical properties to be successfully supplied by the supply method, can be used.

Specifically, in the method for mechanically forming spots using a pin to produce the DNA microarray, the sample containing the immobilization-reinforcing solution must be a sample which adheres to the pin, because the sample is physically retained (adhered) onto the pin to move (supply) the sample onto the base plate. Further, it is necessary that the amount of adhesion is made as uniform as possible for all cases of DNA fragments or the like. Therefore, the selection of immobilization-reinforcing agents that can be mixed with DNA fragments or the like has been extremely restricted.

On the other hand, an ink-jet type spotting method, which is one of non-contact type spotting methods, is known as a method for accurately forming minute spots. A micropipette in which a piezoelectric/electrostrictive element is used as a micropump and a dispenser which is based on the use of the same have been developed and practically used as an apparatus for accurately dispensing a minute amount of biological sample based on the use of the ink-jet type spotting method.

In the non-contact type spotting method, a biological sample, which contains, for example, DNA fragments, nucleic acids, and amino acids, is discharged as minute droplets so that the sample is dropped onto a base plate such as a slide glass.

However, in this method, when the minute droplets of the biological samples, which have relatively high viscosities, are of many different types, and differ only slightly in physical properties, are discharged to the space and dropped onto the slide glass base plate, so-called satellites (splashed droplets finer than objective discharged droplets) tend to appear in addition to the objective droplets (objective discharged droplets). The satellites dropped onto the base plate result in problems of quality of the obtained product. For example, such spots are formed at portions other than original spot formation positions making it impossible to maintain constant spacing distances between the minute spots and causing contamination due to the mixing with each other.

The so-called satellites as described above are not caused at the early stage of the operation of the dispenser in some cases, but the satellites occur after continuing the operation for a certain period of time. An extremely troublesome problem arises in this way in view of the management of production steps. When the discharge speed of the droplets is large, the momentum of the droplets is large upon the dropping onto the slide glass base plate, resulting in a problem such that splashes (mists) are generated forming satellites around the genuine spot.

In order to avoid the occurrence of the so-called satellites as described above, the discharge speed may be decreased. However, if the discharge speed is decreased, the discharge operation becomes unstable.

When the method, in which the hydrophilic polymer or the like is dissolved in the sample containing DNA fragments or the like to reinforce the immobilization of the DNA fragments or the like onto the base plate as described above, is adopted for the ink-jet type spotting method, the sample solution is discharged onto the base plate through a discharge nozzle. However, the solidification of the sample solution may be advanced during the process of discharging the sample solution onto the base plate, resulting in discharge failure. When an immobilization solution having a high viscosity is mixed with the sample to effect the discharge, any discharge defect is likely caused by the drying and solidification of the sample solution in the vicinity of the discharge nozzle.

Further, when it is intended to actually obtain information on the structure or the function of a specimen, the specimen may be bound to the base plate in locations other than the spots. Conventionally, in order to avoid such a phenomenon, a blocking treatment (treatment to avoid any binding of the specimen to portions other than portions at which the spots are formed on the base plate) is performed after forming the spots on the base plate. However, most of captures supplied onto the base plate may flow out during the blocking treatment. Further, the blocking treatment may be incomplete and the S/N ratio of the signal from the spot is deteriorated.

SUMMARY OF THE INVENTION

The present invention has been made taking the foregoing problems into consideration. An object of the present invention is to provide a biochip and a method for producing the same in which a high quality biochip having a high S/N ratio is successfully produced without missing any of the minute spots of a sample containing DNA fragments or the like. This makes it possible to simplify the production steps, reduce the cost, and improve the yield.

According to the present invention, there is provided a biochip comprising a large number of spots based on capture solutions, the spots being arranged on a base plate by supplying, onto the base plate, a plurality of types of the capture solutions to be used to specifically react with a specimen in order to obtain information on a structure or a function of the specimen; wherein a first substance, which acts to immobilize the captures onto the base plate, is formed at least at portions at which the spots are to be formed on the base plate. The solution sample containing the capture herein refers to a solution obtained by dissolving or dispersing the capture in a liquid, which is also referred to as "sample containing the capture solution".

Accordingly, the capture is strongly immobilized onto the base plate. It is possible to prevent the capture from being peeled off, for example, due to the blocking treatment. The first substance, which acts on the immobilization, may be an immobilization solution for immobilizing the captures onto the base plate, or an immobilization-reinforcing solution for reinforcing the immobilization.

The biochip according to the present invention comprises a large number of spots based on samples containing captures, the spots being arranged on a base plate by supplying, onto the base plate, a plurality of types of the samples containing the captures to be used to specifically react with a specimen in order to obtain information on a structure or a function of the specimen; wherein the first substance, which acts on the immobilization of the captures onto the base plate, is formed at least at the portions at which the spots are to be formed on the base plate, and a second substance, which inhibits the immobilization of at least the captures onto the base plate, is formed at parts other than the portions at which the spots are to be formed.

Accordingly, the shape and the arrangement of the spots is determined by the shape of the parts at which the second substance is not formed. Therefore, for example, inconveniences, in which the arrangement spacing between the spots is dispersed and/or the spots are placed close to one another, are avoided when the samples are supplied onto the base plate. If the samples cannot be supplied to prescribed positions, the samples are prevented from contacting with the base plate because of the presence of the second substance. Therefore, no contamination source is brought about thereby. Thus a biochip is obtained, which is excellent in reliability, reproducibility, and quantitative performance when an analysis is performed.

When the sample is supplied in accordance with the ink-jet system, splashes or mists are often generated due to the satellite phenomenon caused when the sample is discharged. Such splashes or mists are prevented from contacting with the base plate because of the presence of the second substance. Therefore, the problem of satellites, which has been caused in the ink-jet system, is successfully eliminated.

In other words, according to the present invention, a high quality biochip can be obtained inexpensively.

As for the biochip constructed as described above, it is preferable that the second substance is a substance which inhibits the immobilization of the captures onto the base plate and which inhibits the contact of the specimen with the base plate. In this case, the substance, which inhibits the contact of the specimen with the base plate, has been already present at its desired location, before the formation of the spots. Therefore, it is unnecessary to perform the blocking treatment for each of the spots after the formation of the spots. Accordingly, it is possible to reliably obtain a large amount of the capture to be immobilized onto the base plate as compared with an ordinary biochip. As a result, the sensitivity to the specimen is improved.

It is also preferable that the first substance is formed on an entire surface of the base plate; and the second substance is formed at parts other than the portions at which the spots are to be formed on the first substance formed on the base plate.

Accordingly, the shape of the parts at which the second substance that determines the shape and the arrangement form of the spots is not formed can be prescribed only by the formation of the second substance. Therefore, a biochip, in which the dispersions of the spacing distance between the spots and the individual shapes are suppressed, is realized. As a result, it is possible to perform an accurate analysis in which the sensitivity to the specimen is uniform.

According to another aspect of the present invention, there is provided a method for producing a biochip comprising a large number of spots based on capture solutions, the spots being arranged on a base plate by supplying, onto the base plate, a plurality of capture solution types to be used to specifically react with a specimen in order to obtain information on a structure or a function of the specimen; the method comprising the step of supplying a solution sample containing the capture and a solution sample containing no capture separately from each other to produce the biochip. In this process, it is preferable that the solution sample containing the capture is supplied in accordance with an ink-jet system.

The solution sample containing no capture herein refers to the solution in which no capture exists in the liquid, which is also referred to as "sample containing no capture solution".

When the sample containing the capture solution and the sample containing no capture solution are supplied separately from each other, the sample containing no capture solution can be selected only in view of the property that the sample containing no capture solution has the ability to reliably immobilize and retain the capture on the base plate, which is preferred. Further, the sample containing the capture solution can be supplied by a supply means which is distinct from a supply means for the sample containing no capture solution. Therefore, it is possible to employ a supply method which is optimum for each of the solutions.

As a result, the following advantage is obtained. That is, the samples containing the capture solutions of several hundreds types or more are sometimes used, while one type of the sample containing no capture solution is usually used in many cases. In such circumstances, it is possible to adopt the means with which a large amount of the sample can be treated conveniently and inexpensively, as the supply means for the sample containing no capture solution.

When the ink-jet system is used as the supply means for the sample containing the capture solution, a minute amount of the sample containing the capture solution can be accurately supplied onto the base plate. The ink-jet system is a non-contact type liquid supply system. Therefore, the ink-jet system is most appropriate when one spot is formed by supplying two or more types of solutions of the sample containing the capture solution and the sample containing no capture solution, for the following reason.

That is, except for the case of certain limited research experiments, a plurality of biochips are usually produced at once. The sample containing the identical capture solution is supplied a plurality of times to a plurality of base plates. In such a situation, for example, if the sample is supplied while making contact with the base plate as in the pin system, the sample containing the capture solution and the sample containing no capture solution are mixed with each other at the pin tip. The mixing rate is changed every time when the supply is performed. As a result, such a procedure causes any dispersion of the amount of capture supplied to each of the spots of each of the biochips. Such a problem is completely excluded by adopting the non-contact type liquid supply system such as the ink-jet system.

Further, in the ink-jet system, for example, the discharge amount and the momentum of discharge (discharge speed) can be accurately controlled electrically. Therefore, it is also possible to intentionally change the ratio between the sample containing the capture solution and the sample containing no capture solution for each spot. The ink-jet system is advantageous to improve the quality.

Further, in the present invention, it is preferable that the sample containing no capture solution is supplied to the base plate in accordance with an ink-jet system or a screen printing system. When the sample is supplied in accordance with the ink-jet system, then the sample containing no capture solution can be supplied accurately in a minute amount in the same manner as the sample containing the capture solution described above, and the both solutions can be supplied in a well-controlled manner without any dispersion of the mixing rate of the both solutions. Thus, the quality of the biochip is improved.

When the sample is supplied in accordance with the screen printing system, the sample can be supplied inexpensively and quickly in a large amount with sufficient accuracy for the ordinary biochip in which about several thousands of spots are formed per one sheet, although the amount and the position cannot be accurately controlled as compared with the ink-jet system.

The supply of the sample containing no capture solution is not limited to the ink-jet system and the screen printing system. The sample may be supplied, for example, in accordance with the dipping system or the spray system by effecting the patterning with a mask, if necessary.

In this case, the sample containing no capture solution may be an immobilization solution for immobilizing the sample containing the capture solution onto the base plate, or an immobilization-reinforcing solution for reinforcing immobilization.

Accordingly, at first, when the sample containing the capture is supplied, the immobilization solution is also supplied. Therefore, it is unnecessary to previously supply (or coat in common cases) the immobilization solution onto the base plate. It is possible to prevent the increase in cost of the base plate beforehand. Further, both of the supply of the immobilization solution and the supply of the sample containing the capture are performed within a relatively short period of time. Therefore, it is possible to suppress the occurrence of dispersion of the quality of the biochip due to the time-dependent change of the immobilization solution, unlike a case in which the immobilization solution is previously supplied onto the base plate.

Further, it is unnecessary to perform the step of mixing the sample and the immobilization-reinforcing solution, because the sample and the immobilization-reinforcing solution are supplied separately from each other. Further, it is enough to use a slight amount of the immobilization-reinforcing solution which is necessary to reinforce the immobilization of the minute amount of sample supplied onto the base plate. Therefore, it is possible to greatly decrease the amount of the immobilization-reinforcing solution. This procedure is advantageous to simplify the production steps and reduce the cost.

When the ink-jet system is adopted, it is unnecessary to conform the nozzle for supplying the immobilization solution or the immobilization-reinforcing solution to the supply specification for the sample containing the capture. The nozzle can be designed exclusively (for example, to have a structure which is hardly dried). Thus, it is possible to improve the degree of freedom of the design.

Further, even when the immobilization solution or the immobilization-reinforcing solution is a liquid which is apt to be dried or solidified, the sample is not solidified during the supply of the sample containing the capture. Therefore, it is possible to supply the sample with enough time margin. Therefore, the sample and the immobilization solution can be supplied while considering, for example, the positioning for the supply portion including the capture, the supply timing depending on the type of the sample, and the supply amount. It is possible to improve the quality of the biochip and improve the yield.

Especially, it is preferable that the immobilization solution or the immobilization-reinforcing solution is a solution with which immobilization or immobilization reinforcement is advanced by mixing the immobilization solution or the immobilization-reinforcing solution with the sample containing the capture. In this case, the sample and the immobilization solution can be supplied with more sufficient time margin. This procedure contributes to the improvement in yield.

When the sample containing the capture and the immobilization solution or the immobilization-reinforcing solution are supplied separately from each other, then the immobilization solution or the immobilization-reinforcing solution may be supplied onto the base plate, and then the sample containing the capture may be supplied to parts to which the immobilization solution or the immobilization-reinforcing solution has been supplied. Inversely, the sample containing the capture may be supplied onto the base plate, and then the immobilization solution or the immobilization-reinforcing solution may be supplied to parts to which the sample containing the capture has been supplied. Alternatively, the both may be supplied substantially simultaneously.

When the immobilization solution or the immobilization-reinforcing solution is previously supplied onto the base plate, the solution physically intervenes between the capture and the base plate. Thus, the immobilization is further strengthened. However, the immobilization-reinforcing agent persistently reinforces the immobilization. Therefore, it is preferable to use those which exert less influence to inhibit the physical contact between the capture and the base plate or between the capture and the immobilization solution on the base plate. It is recommended to use a polymer type substance having a structure including many three-dimensional interstices.

When the immobilization solution or the immobilization-reinforcing solution is supplied after the sample containing the capture is supplied, the solution is consequently supplied onto the portion to which the sample containing the capture has been accurately supplied beforehand. It is unnecessary to strictly prescribe the positioning accuracy when the immobilization solution or the immobilization-reinforcing solution is supplied. Therefore, it is possible to increase the yield inexpensively. In this case, it is required to use the immobilization solution or the immobilization-reinforcing solution having a structure and a thickness so that the action of the capture to capture the specimen is not inhibited.

Further, when the sample containing the capture and the immobilization solution or the immobilization-reinforcing solution are supplied substantially simultaneously, the supply time can be shortened, which is preferred. This procedure can be achieved in accordance with the ink-jet system which is a non-contact type supply system.

It is preferable that the captures are nucleic acids. Further, it is preferable that the nucleic acid is DNA and/or fragment thereof or amplified product thereof; cDNA and/or fragment thereof or amplified product thereof; RNA or antisense RNA and/or fragment thereof or amplified product thereof; chemically synthesized DNA or amplified product thereof; or chemically synthesized RNA or amplified product thereof.

It is preferable that the captures are proteins. Further, it is preferable that the protein is antigen, antibody, lectin, adhesin, receptor for physiologically active substance, or peptide.

It is preferable that the immobilization solution is a solution of chemical substance having positive charge, and the capture is immobilized by means of ionic bond. That is, the following forms are preferred: the chemical substance is a silane coupling agent such as γ-aminopropyltriethoxysilane, poly-L-lysine, or polyalkylamine; or the immobilization solution includes a chemical substance for chemically modifying a base plate surface, and a functional group introduced into the base plate surface and a functional group introduced by modifying the capture are subjected to a chemical reaction to immobilize the capture onto the base plate by means of covalent bond; i.e., the chemical reaction is a reaction of amino group and aldehyde group, a reaction of amino group and N-hydroxysuccinimido group, a reaction of amino group and carboxyl group, a reaction of amino group and epoxy group, or a reaction of thiol group and epoxy group. Alternatively, the following forms are preferred: the immobilization solution generates affinity bond or hydrogen bond for the capture with respect to the base plate; i.e., the immobilization solution includes avidin, streptavidin, protamine, or histone. Further alternatively, the following forms are preferred: the immobilization solution generates hydrophobic bond for the capture with respect to the base plate; i.e., the immobilization solution is a solution containing hydrophobic group such as phenyl group of hydrophobic substance such as polystyrene and alkyl group of alkylbenzene or the like.

Further, the following forms are preferred: the immobilization-reinforcing solution includes a water-retentive substance; i.e., the water-retentive substance is colominic acid, hyaluronic acid, or mixture of colominic acid and hyaluronic acid. Alternatively, the following forms are preferred: the immobilization-reinforcing solution includes a high-molecular substance; i.e., the highmolecular substance is acidic polymer such as CM-cellulose, nitrocellulose, polyacrylic acid, and alginic acid; basic polymer such as polyethyleneimine and polyacrylamide; neutral polymer such as methyl cellulose, polyethylene glycol, and polypropylene glycol; or protein such as BSA, egg albumin, and lysozyme.

When the substances of the capture, the immobilization solution, and the immobilization-reinforcing solution are combined as described above, the immobilization of the capture onto the base plate is strengthened. Further, when this feature is combined with the method in which the solution containing the capture and the solution containing no capture, i.e., the immobilization solution or the immobilization-reinforcing solution are supplied onto the base plate separately from each other in accordance with the basic concept of the present invention, the immobilization proceeds in a form in which the orientation is made uniform for the captures, i.e., the captures are spread over the base plate three-dimensionally. It is easy for the capture to capture the specimen. As a result, the quality of the biochip is improved.

Further, when the solutions are supplied separately from each other, the functions of the immobilization solution and the immobilization-reinforcing solution are prevented from deteriorating which would be otherwise caused by any influence exerted by drying or the like brought about by being exposed to the atmosphere. Accordingly, it is preferred that the solutions are supplied onto the base plate while retaining the original functions of the foregoing substances.

Further, when the water-retentive substance is used for the immobilization-reinforcing solution, as preferred, the immobilization reaction for the capture to be immobilized on the base plate can be sufficiently advanced over a period of time by retaining water in the spots.

Further, when the high-molecular substance is used for the immobilization-reinforcing solution, as preferred, then the capture is freely movable in the immobilization-reinforcing solution, and the immobilization or the capture of the specimen by the capture is not inhibited.

Especially, the capture is preferably prepared by performing the steps of PCR-amplifying DNA fragments to prepare PCR product, drying the PCR product to obtain DNA powder, and dissolving the DNA powder in a buffer solution. When the PCR amplification step is performed, a variety of functional groups to facilitate immobilization can be added to DNA fragments, which is preferred for the present invention.

Preferably, the present invention further comprises preparing a jig to which a plurality of the base plates are set, wherein the sample containing the capture solution and the sample containing no capture solution are supplied in a state in which the base plates are fixed on the jig. The setting of the base plates is not subjected to resetting every time when the solution is supplied. Accordingly, it is possible to reduce the production cost. On the other hand, an advantage is simultaneously obtained such that it is possible to reduce the discrepancy of the positions to which two solutions are to be supplied.

Further, the method for producing the biochip according to the present invention has such a feature that an area, in which the sample containing no capture solution is supplied onto the base plate, is substantially the same as an area to which the sample containing the capture solution is supplied, or an area which includes the area to which the sample containing the capture solution is supplied, the area having a substantially circular shape.

Accordingly, the shape of the spot, in which each of the captures of the biochip exists, is determined by the spot shape of the sample containing no capture solution. Therefore, it is possible to eliminate the deviation of the spot shape which would be otherwise caused by the difference in the type of the capture.

The procedure can be successfully managed with one type of supply means (pin or ink-jet discharge unit) as well, because one type of the sample containing no capture solution is supplied. Therefore, it is also possible to eliminate the dispersion of the spot shape which would be otherwise caused by the difference in the supply means. Further, the size of each of the spot shapes of the biochip is determined by the amount of supply of the sample containing no capture, and the amount can be made larger than the amount of supply of the sample containing the capture solution. As a result, it is possible to reduce the amount of supply of the sample containing the capture solution to realize the size of the spot required for the biochip.

In the case of the ordinary method for producing the biochip in the present circumstances, almost all of the amount of the sample containing the capture solution supplied onto the base plate is washed out without being immobilized onto the base plate. On the contrary, in the present invention, the sample containing the capture solution is diffused up to a supply area formed by the sample containing no capture solution. Therefore, the sample is immobilized more efficiently on the base plate. It is possible to decrease the amount of being washed out without being immobilized.

Further, the production method as described above is preferred when the sample containing the capture solution is supplied in accordance with the ink-jet method. In this procedure, even when satellites are generated when the sample containing the capture solution is supplied as described above, the satellites scarcely arrive at the sample solution area containing no capture. Even if the satellites arrive at the sample solution area containing no capture, the satellites are integrated into the regular sample. As a result, it is possible to avoid almost all of the satellite problem.

This positive effect is exerted on more than just the satellite problem. The same or equivalent effect is also exhibited for the "problem of so-called flight curvature resulting in dispersion of discharge direction" which possibly may be caused with the ink-jet system.

Further, in the present invention, the method for producing the biochip may have such a feature that an area, in which the sample containing no capture solution is supplied onto the base plate, has a size which includes two or more areas to each of which the sample containing the capture solution is supplied. In this case, the sample containing no capture solution is supplied more conveniently.

According to still another aspect of the present invention, a method is provided for producing a biochip comprising the steps of providing a first substance, which immobilizes the captures onto said base plate at least where the spots are to be formed, and forming a second substance for inhibiting immobilization of the captures onto the base plate at parts where the spots are not to be formed.

Accordingly, the solution containing the capture is spotted onto the base plate where the first substance is already formed at the portions to be spotted and the second substance is formed at the portions other than the above. The shape and the arrangement of the spots are determined by the shape of the parts where the second substance is not formed. For example, inconveniences, in which the arrangement spacing between the spots is dispersed and the spots are placed close to one another, disappear. Further, when the sample cannot be supplied to the prescribed position, the sample is prevented from contacting with the base plate because of the presence of the second substance. Therefore, no contamination source is generated. Splashes or mists, which are caused by the satellite phenomenon often caused during the discharge of the sample when the sample is supplied in accordance with the ink-jet system, are prevented from contacting with the base plate because the presence of the second substance. Therefore, it is possible to eliminate the problem of satellites having been caused by the ink-jet system. The present invention is advantageous as described above, it is possible to produce the high quality biochip. It is possible to simplify the production steps, reduce the cost, and improve the yield.

It is preferable that the production method described above further comprises the steps of forming the first substance at the portions at which at least the spots are to be formed on the base plate; and forming the second substance at the parts other than the portions at which the spots are to be formed on the base plate. When the method comprises the step of forming the first substance and the step of forming the second substance, then the materials can be selected while taking the compatibility of each of the substances into consideration, and the formation timing can be individually adjusted. Thus, it is possible to extract the characteristics of each of the substances to the maximum.

It is also preferable that the production method described above further comprises the steps of forming the first substance on an entire surface of the base plate; and forming the second substance at parts other than the portions at which the spots are to be formed, on the first substance formed on the base plate. When the first substance is formed on the entire surface, it is possible to adopt the steps of mass production in which the cost is further suppressed.

It is also preferable that the production method described above further comprises the steps of using, as the base plate, a base plate on which the first substance is previously formed at the portions at which the spots are to be formed; and forming the second substance at parts other than the portions at which the spots are to be formed on the base plate.

It is also preferable that the second substance is a substance which inhibits the immobilization of the captures onto the base plate and which inhibits the contact of the specimen with the base plate.

It is also preferable that the sample containing the capture is supplied in accordance with an ink-jet system. In this procedure, the sample can be supplied efficiently at a high speed. Further, the sample is supplied in accordance with the non-contact system in which the supply means makes no contact with the base plate. Therefore, it is possible to avoid such a problem that the second substance, which is previously formed on the base plate, is mixed into the sample supply means to cause the contamination.

When the sample is supplied in accordance with the ink-jet system, the high speed supply can be realized. However, the satellite phenomenon is often caused during the discharge of the sample, and the base plate is polluted in some cases. However, splashes or mists, which are caused by the satellite phenomenon, are prevented from contacting with the base plate owing to the presence of the second substance. Therefore, the problem of satellites, which has been caused in the ink-jet system, is successfully eliminated. Therefore, the supply of the sample in accordance with the ink-jet system can be actively facilitated.

It is also preferable in the production method described above that the first step includes a treatment for forming the first substance on the entire surface of the base plate; and the second step includes a treatment for forming the second substance at parts other than the portions at which the spots are to be formed, on the first substance.

In this case, it is also preferable that the second substance is supplied in accordance with an ink-jet system. When the second substance is formed at the parts other than the portions at which the spots are to be formed, it is possible to improve both of the positional accuracy and the thickness accuracy. It is possible to clearly discriminate the shape of the boundary between the parts at which the spots are to be formed and the parts other than the portions at which the spots are to be formed. Further, the second substance can be supplied efficiently without any loss. Therefore, the method contributes to the reduction of the production cost.

It is also preferable that the second substance is formed in accordance with a screen printing method. In this case, it is possible to shorten the supply time for the second substance to the parts other than the portions at which the spots are to be formed. It is possible to improve the throughput and reduce the number of steps.

It is also preferable that the second substance is formed in accordance with a dipping method. In this case, it is also preferable that a resist is formed at the portions at which the spots are to be formed, on the first substance formed on the base plate; the second substance is formed on an entire surface including the resist in accordance with the dipping method; and the resist is subjected to lift-off to form the second substance at parts other than the portions at which the spots are to be formed.

The method based on the dipping is preferably adopted when the second substance has a low viscosity. Also in this case, it is possible to shorten the supply time for the second substance to the parts other than the portions at which the spots are to be formed. It is possible to improve the throughput and reduce the number of steps.

When the first substance is a chemical substance having positive charge to act on the immobilization of the captures onto the base plate by means of ionic bond; the second substance is a chemical substance having negative charge.

In this case, it is preferable that the first substance includes at least a silane coupling agent such as γ-γ-aminopropyltriethoxysilane, poly-L-lysine, polyethyleneimine, or polyalkylamine; and the second substance includes at least organic acid such as succinic acid, gluconic acid, glycolic acid, malic acid, and acrylic acid; synthetic high-molecular acid such as polyacrylic acid, polylactic acid, dextran sulfate, and polyglycolic acid; or natural high-molecular acid such as alginic acid, polygalacturonic acid, hyaluronic acid, and chondroitin sulfuric acid.

The combination, in which the first substance is the chemical substance having positive charge and the second substance is the chemical substance having negative charge, is preferably adopted when the capture has negative charge and the immobilization onto the base plate is performed by means of ionic bond. However, when the capture has no negative charge, a combination may be also available, in which the first substance is a chemical substance having negative charge and second substance is a chemical substance having positive charge.

When the first substance is a chemical substance having an active group for modifying a base plate surface to act on the immobilization of the captures onto the base plate by means of covalent bond by effecting a chemical reaction of the active group introduced into the base plate surface and a functional group introduced by modifying the captures; the second substance is a chemical substance having the functional group reactive with the active group.

In this case, the chemical reaction to achieve the covalent bond is a reaction of amino group and aldehyde group, a reaction of amino group and N-hydroxysuccinimido group, a reaction of amino group and carboxyl group, a reaction of amino group and epoxy group, or a reaction of thiol group and epoxy group.

It is preferable that the first substance includes at least a mixture of γ-aminopropyltriethoxysilane and glutaraldehyde, a mixture of γ-aminopropyltriethoxysilane, succinic anhydride, and N-hydroxysuccinimido, a mixture of γ-aminopropyltriethoxysilane and succinic anhydride, epichlorohydrin, or bisoxysilane; and the second substance includes at least amino acid such as glycine, tris having amino group, ethanolamine, cysteine having thiol group, glutathione, or thioglycol.

When the first substance is a chemical substance for modifying a base plate surface to act on the immobilization of the captures onto the base plate by means of affinity bond; the second substance is a substance which makes the affinity bond with the chemical substance.

In this case, it is preferable that the first substance includes at least avidin, streptavidin, protamine, histone, biotin, antigen, antibody combining protein, or antibody; and the second substance includes at least avidin, streptavidin, biotin, nucleic acid, antigen, antibody combining protein, or antibody.

When the first substance is a chemical substance including hydrophobic group such as styrene group, phenyl group, and alkyl group for modifying a base plate surface to act on the immobilization of the captures onto the base plate by means of hydrophobic bond; the second substance includes at least an amphiphilic substance.

In this case, it is preferable that the first substance includes at least polystyrene or alkylbenzene; and the second substance includes at least gelatin or casein.

It is preferable that the second substance is composed of a substance having water repellency including, for example, silicon or fluorine. In general, the biological substance such as the sample containing the capture is in a form of aqueous solution in many cases. When the substance, which has the water repellency or the hydrophobicity, is selected as the second substance, the effect is further enhanced to inhibit the immobilization of the capture onto the base plate. Further, the sample solution (sample solution containing the specimen), which is employed when the biochip is used, is also in a form of aqueous solution in many cases. In such a situation, the nonspecific binding of the sample to the portions other than the spots is effectively suppressed by the repelling force with respect to the portions at which the second substance is formed other than the spots. Thus, the S/N ratio of the signal of the spot is improved.

It is also preferable that the captures are nucleic acids. In this case, the nucleic acid is exemplified by DNA and/or fragment thereof or amplified product thereof; cDNA and/or fragment thereof or amplified product thereof; RNA or antisense RNA and/or fragment thereof or amplified product thereof; chemically synthesized DNA or amplified product thereof; or chemically synthesized RNA or amplified product thereof.

It is also preferable that the captures are proteins. In this case, the protein is exemplified by antigen, antibody, lectin, adhesin, receptor for physiologically active substance, or peptide.

The above and other objects, features, and advantages of the present invention will become more apparent from the following description when taken in conjunction with the accompanying drawings in which a preferred embodiment of the present invention is shown by way of illustrative example.

DESCRIPTION OF THE PREFERRED EMBODIMENTS

Illustrative embodiments of the biochip and the method for producing the same according to the present invention will be explained below with reference to FIGS. 1 to 16C.

Figure 1:
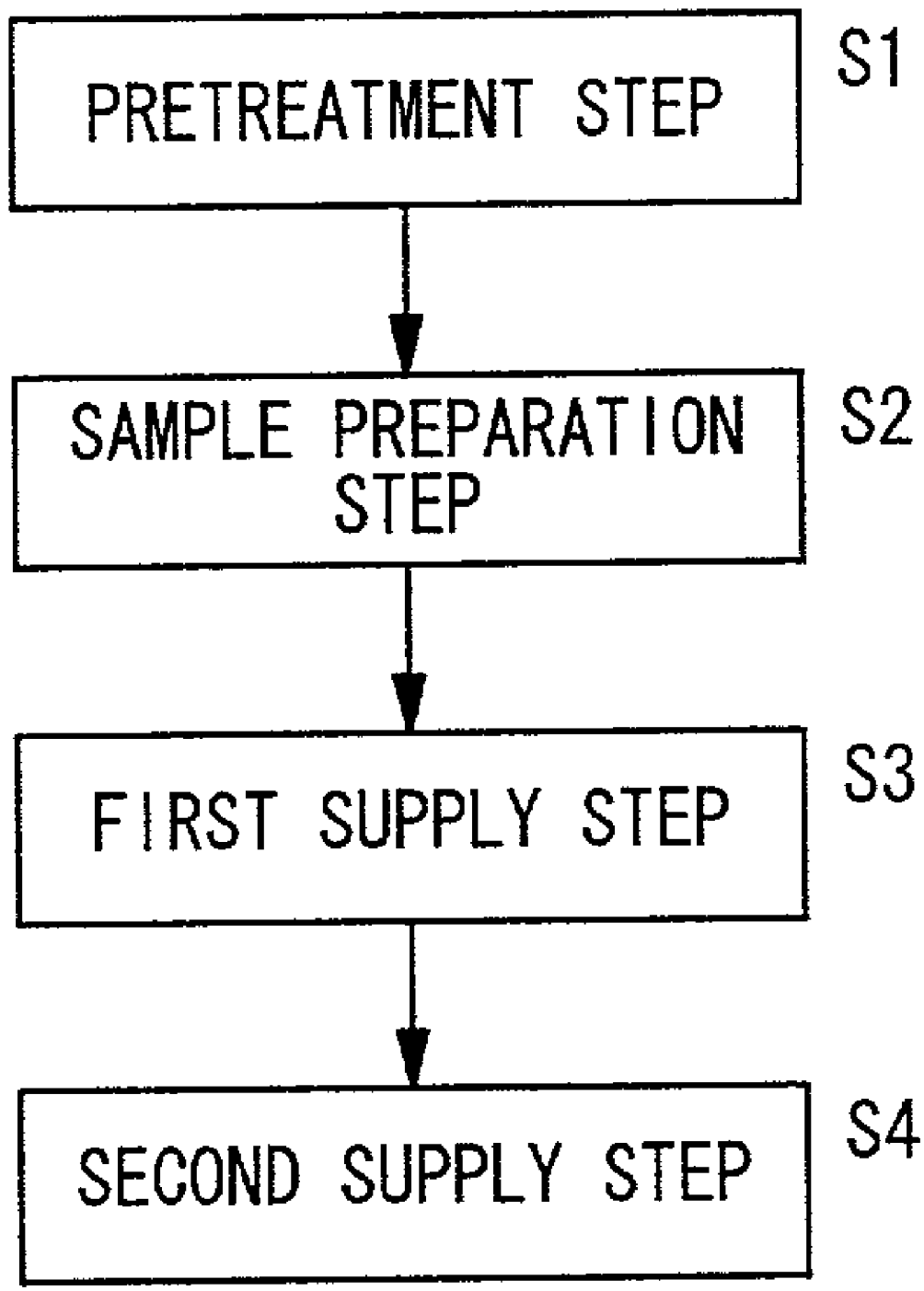
FIG. 1 is a block diagram illustrating steps of a method for producing a biochip according to a first embodiment.
Figure 3:
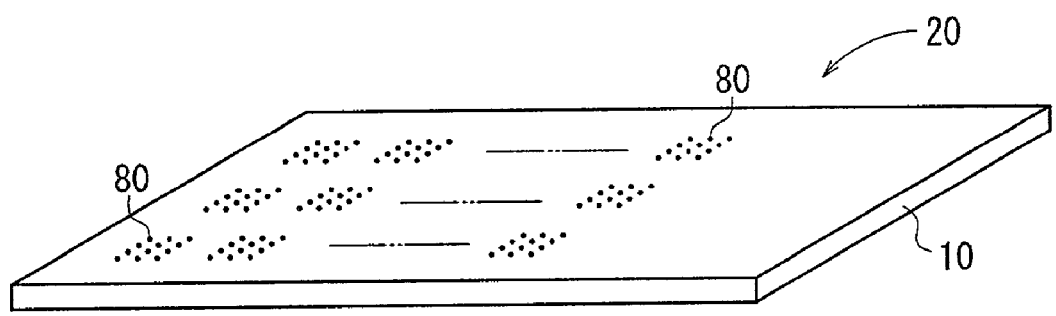
FIG. 3 is a perspective view illustrating the biochip to be produced.

At first, as shown in FIG. 1, a method for producing a biochip according to a first embodiment comprises a pretreatment step S1 of forming a poly-L-lysine layer 12 (see FIGS. 4A to 4C) on the surface of a base plate 10, a sample preparation step S2 of preparing a sample containing DNA fragments, a first supply step S3 of supplying (including dropping) an immobilization-reinforcing solution onto the base plate 10, and a second supply step S4 of supplying (including dropping) the sample obtained in the sample preparation step S2 onto the immobilization-reinforcing solution having been supplied onto the base plate 10 to produce the biochip 20 shown in FIG. 3.

Figure 2:
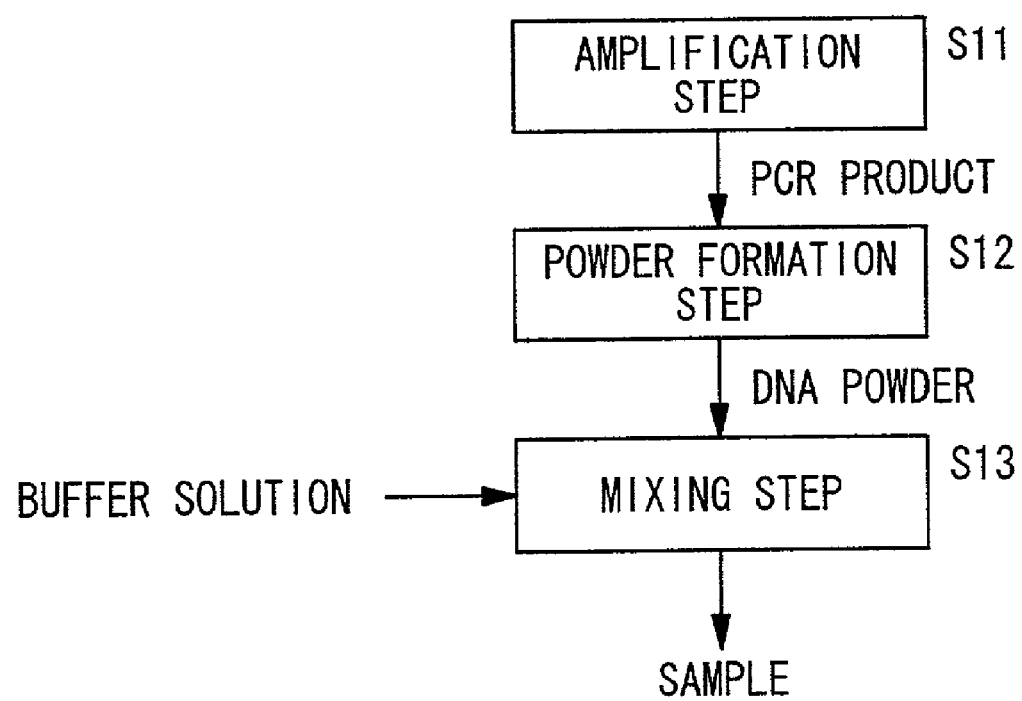
FIG. 2 is a block diagram illustrating steps as contents of a sample preparation step.

As shown in FIG. 2, the sample preparation step S2 includes an amplification step S11 of performing PCR amplification for the DNA fragments to prepare a PCR product, a powder formation step S12 of drying the obtained PCR product to prepare DNA powder, and a mixing step S13 of dissolving the obtained DNA powder in a buffer solution.

The process will be specifically explained below. That is, in the pretreatment step S1, the base plate 10 is firstly immersed in an alkaline solution to perform slow shaking at room temperature for at least 2 hours. The alkaline solution is a solution which is obtained, for example, by dissolving NaOH in distilled water, and adding ethanol thereto, followed by being agitated until the solution is completely transparent.

After that, the base plate 10 is taken out, is transferred into distilled water, and is rinsed to remove the alkaline solution. Subsequently, the base plate 10 is immersed in a poly-L-lysine solution prepared by adding poly-L-lysine to distilled water, followed by being left to stand for 1 hour.

After that, the base plate 10 is taken out, and it is applied to a centrifugal machine to perform centrifugation so that any excessive poly-L-lysine solution is removed. Subsequently, the base plate 10 is dried at 40° C. for about 5 minutes to obtain the base plate 10 with the poly-L-lysine layer 12 formed on the surface.

Subsequently, the sample preparation step S2 is performed. At first, 3 M sodium acetate and isopropanol are added to the PCR product amplified by using a known PCR machine (amplification step S11), followed by being left to stand for several hours. After that, the PCR product solution is centrifuged with a centrifugal machine to precipitate the DNA fragments.

The precipitated DNA fragments are rinsed with ethanol, followed by centrifugation. After that, the DNA fragments are dried to produce the DNA powder (powder formation step S12). A TE buffer solution is added to the obtained DNA powder, followed by being left to stand for several hours to completely dissolve the DNA powder (mixing step S13). Thus, the sample is prepared. The concentration of the sample at this stage is 0.1 to 10 μg/μ liter.

Figure 4A:
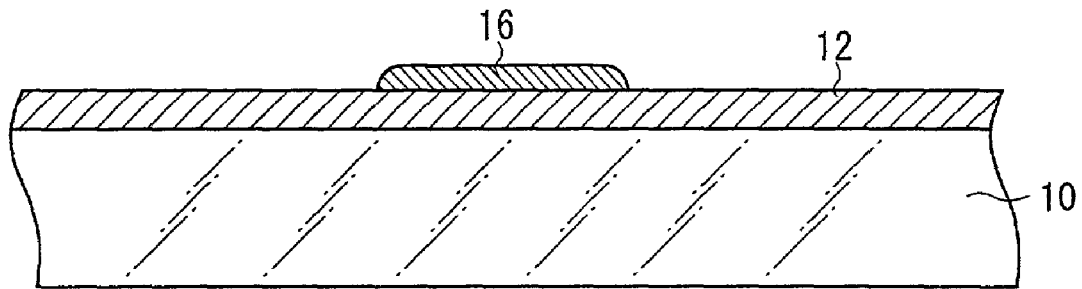
FIG. 4A shows a step illustrating a state in which an immobilization-reinforcing solution is supplied onto a base plate.

In this embodiment, as shown in FIG. 4A, the immobilization-reinforcing solution 16 is supplied onto the base plate 10

Figure 4B:
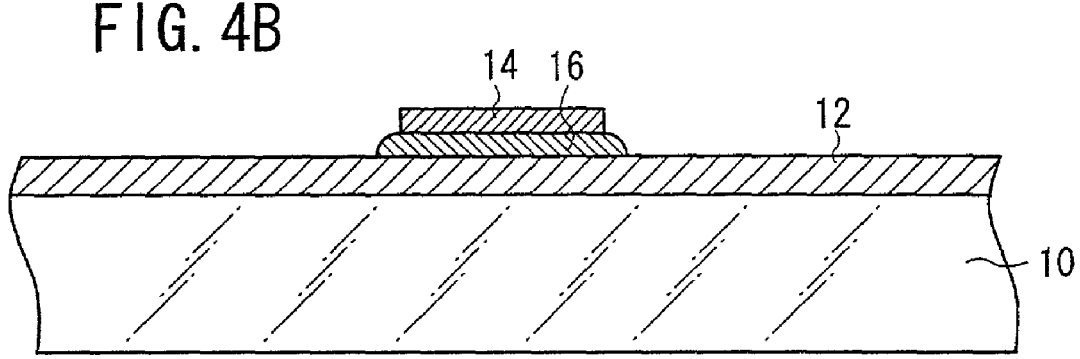
FIG. 4B shows a step illustrating a state in which a sample is supplied onto the immobilization-reinforcing solution on the base plate.
Figure 4C:
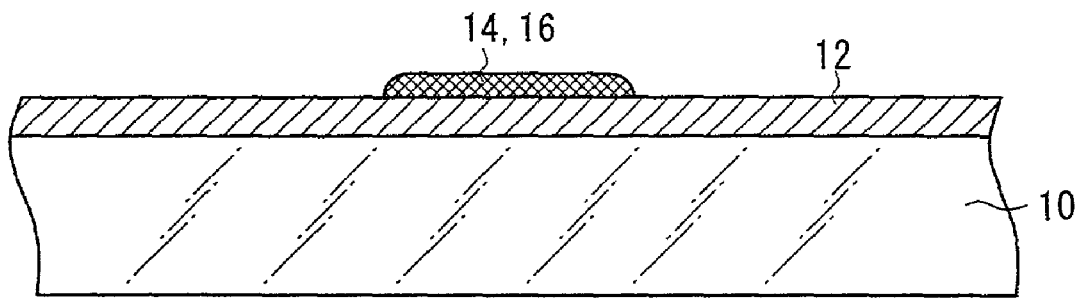
FIG. 4C shows a step illustrating a state in which the sample and the immobilization-reinforcing solution are integrated into one unit.

(first supply step S3). Subsequently, as shown in FIG. 4B, the sample 14, which is obtained in the sample preparation step S2, is supplied onto the immobilization-reinforcing solution 16 having been supplied onto the base plate 10. Accordingly, the biochip 20 shown in FIG. 3 is produced (second supply step S4). The supply area for the sample 14 is made smaller than the area to which the immobilization-reinforcing solution 16 has been supplied, by adjusting the supply amount. The sample 14 may be diluted depending on the type of the sample 14. Organic polymer is used for the immobilization-reinforcing solution 16. The sample 14 promptly diffused in the immobilization-reinforcing solution 16 after the supply, and the sample 14 is uniformly dispersed in the area prescribed by the immobilization-reinforcing solution 16 as shown in FIG. 4C.

Figure 5A:
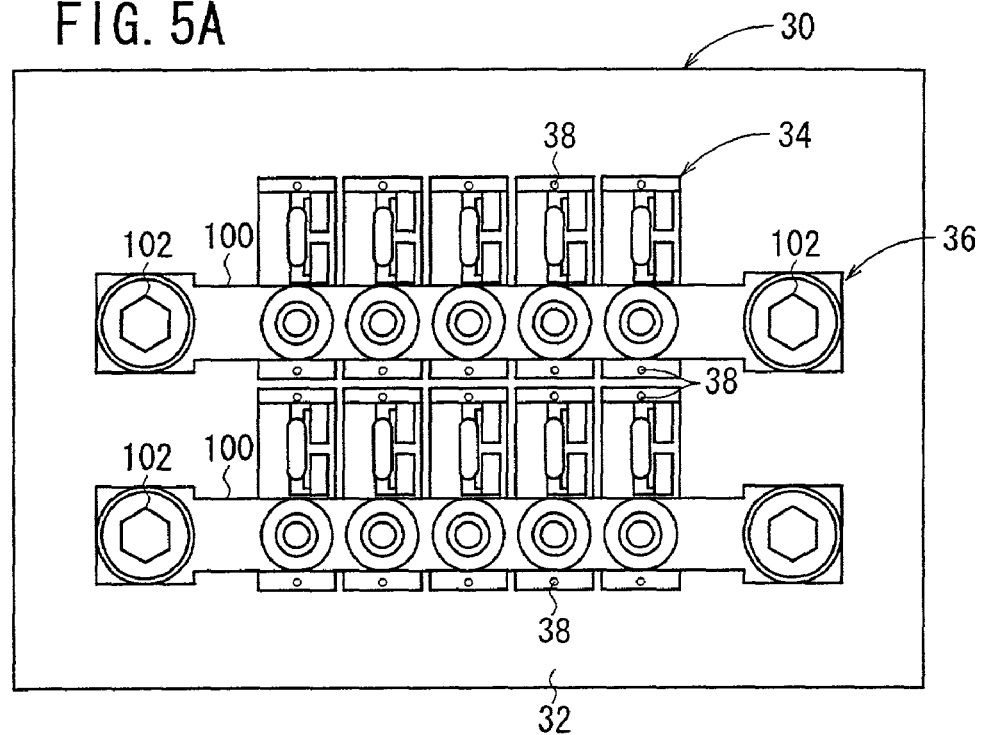
FIG. 5A is a plan view illustrating an arrangement of a dispenser to be used for the method for producing the biochip according to the first embodiment.
Figure 5B:
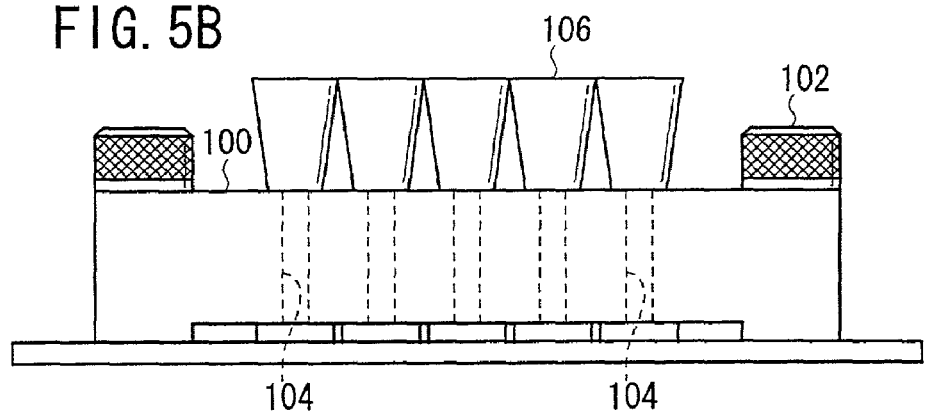
FIG. 5B is a front view thereof.

Especially, in this embodiment, a disperser 30 as shown in FIG. 5A is used for the first supply step S3 and the second supply step S4.

The dispenser 30 has the following arrangement. That is, for example, ten micropipettes 34 are arranged in five rows and two columns on an upper surface of a fixation plate 32 having a rectangular configuration. A group of the micropipettes 34 arranged in the direction of each column are fixed on the fixation plate 32 by the aid of a fixing jig 36 respectively.

Figure 5C:
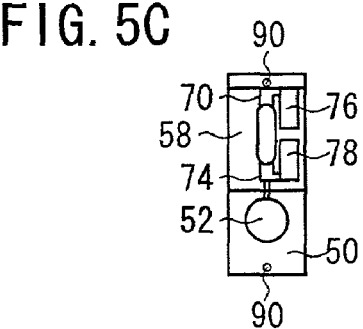
FIG. 5C is a magnified plan view illustrating one micropipette of the dispenser.
Figure 6:
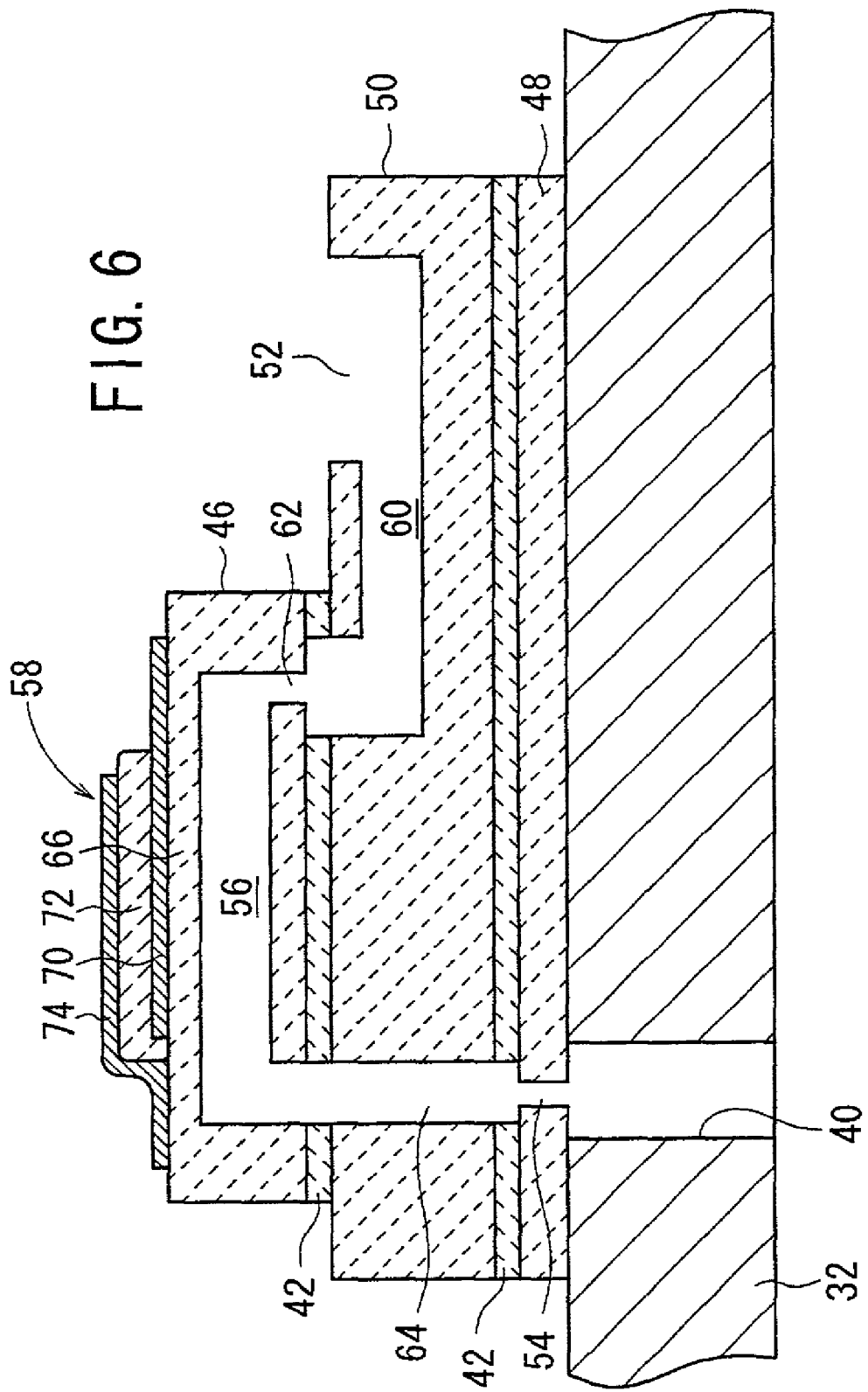
FIG. 6 is a longitudinal sectional view illustrating an arrangement of the micropipette.

As shown in FIGS. 5C and 6, the micropipette 34 comprises a sample-pouring port 52 which is formed at the upper surface of a substrate 50 having a substantially rectangular parallelepiped-shaped configuration, a sample discharge port 54 which is formed at the lower surface of the substrate 50, a cavity 56 which is formed at the inside between the sample-pouring port 52 and the sample discharge port 54, and an actuator section 58 which is used to vibrate the substrate 50 or change the volume of the cavity 56.

Therefore, as shown in FIG. 6, through-holes 40 are provided through the fixation plate 32 at portions corresponding to the sample discharge ports 54 of the micropipettes 34 respectively. Accordingly, the sample 14 or the immobilization-reinforcing solution 16, which is discharged from the sample discharge port 54 of the micropipette 34, is supplied through the through-hole 40, for example, to the base plate 10 which is fixed under the fixation plate 32.

An introducing bore 60 having a substantially L-shaped configuration with a wide opening width is formed over a region ranging from the sample-pouring port 52 to the inside of the substrate 50 in the micropipette 34. A first communication hole 62 having a small diameter is formed between the introducing bore 60 and the cavity 56. The sample 14 or the immobilization-reinforcing solution 16, which is poured from the sample-pouring port 52, is introduced into the cavity 56 through the introducing bore 60 and the first communication hole 62.

A second communication hole 64, which communicates with the sample discharge port 54 and which has a diameter larger than that of the first communication hole 62, is formed at a position different from that of the first communication hole 62, of the cavity 56. In the embodiment of the present invention, the first communication hole 62 is formed at the portion of the lower surface of the cavity 56 deviated toward the sample-pouring port 52. The second communication hole 64 is formed at the position of the lower surface of the cavity 56 as well corresponding to the sample discharge port 54.

Further, in this embodiment, the portion of the substrate 50, with which the upper surface of the cavity 56 makes contact, is thin-walled to give a structure which tends to undergo the vibration with respect to the external stress so that the portion functions as a vibrating section 66.

The substrate 50 is constructed by laminating a plurality of green sheets made of zirconia ceramics, followed by being sintered into one unit.

That is, the substrate 50 is constructed by laminating a layer which is formed with a window of the sample-pouring port 52 and which is partially formed with a plurality of windows as a part of the introducing bore 60 and a part of the second communication hole 64 respectively, a layer which is formed with a plurality of windows as a part of the introducing bore 60 and a part of the second communication hole 64 respectively, and a layer which is formed with a window as a part of the second communication hole 64, followed by being sintered into one unit.

The actuator section 58 comprises a base 46 composed of zirconia ceramics constructed by laminating a layer which is partially formed with a plurality of windows as parts of the first communication hole 62 and the second communication hole 64 respectively, a layer which is formed with the cavity 56, and a layer which is provided to form the vibrating section 66, followed by being sintered into one unit in the same manner as in the substrate 50, a lower electrode 70 which is directly formed on the vibrating section 66, a piezoelectric layer 72 which is composed of, for example, a piezoelectric/electrostrictive layer or an anti-ferroelectric layer formed on the lower electrode 70, and an upper electrode 74 which is formed on the upper surface of the piezoelectric layer 72.

As shown in FIG. 5C, the lower electrode 70 and the upper electrode 74 are electrically connected to an unillustrated driving circuit via a plurality of pads 76, 78 which are formed on the upper surface of the base 46 respectively.

A nozzle sheet 48 is formed with the sample discharge port 54. The sample discharge port 54 is formed through a resin film using an excimer laser.

The micropipette 34 constructed as described above is operated as follows. That is, when an electric field is generated between the upper electrode 74 and the lower electrode 70, the piezoelectric layer 72 is deformed. The vibrating section 66 is then deformed in accordance therewith. Accordingly, the volume of the cavity (pressurizing chamber) 56 contacting with the vibrating section 66 is decreased.

When the volume of the cavity 56 is decreased, the sample 14 or the immobilization-reinforcing solution 16 charged in the cavity 56 is discharged at a predetermined speed from the sample discharge port 54 which communicates with the cavity 56. As shown in FIG. 3, it is possible to prepare the biochip 20 in which the sample 14 and the immobilization-reinforcing solution 16 discharged from the micropipettes 34 are aligned and fixed as minute spots 80 on the base plate 10 such as a microscopic slide glass.

An apparatus structure based on the so-called ink-jet system may be adopted as the structure in which the volume of the cavity 56 is decreased in accordance with the driving of the actuator section 58 (see Japanese Laid-Open Patent Publication No. 6-40030).

The cavity (pressurizing chamber) 56 is formed to have such a flow passage dimension that the sample 14 containing DNA fragments or the like is moved.

Figure 7:
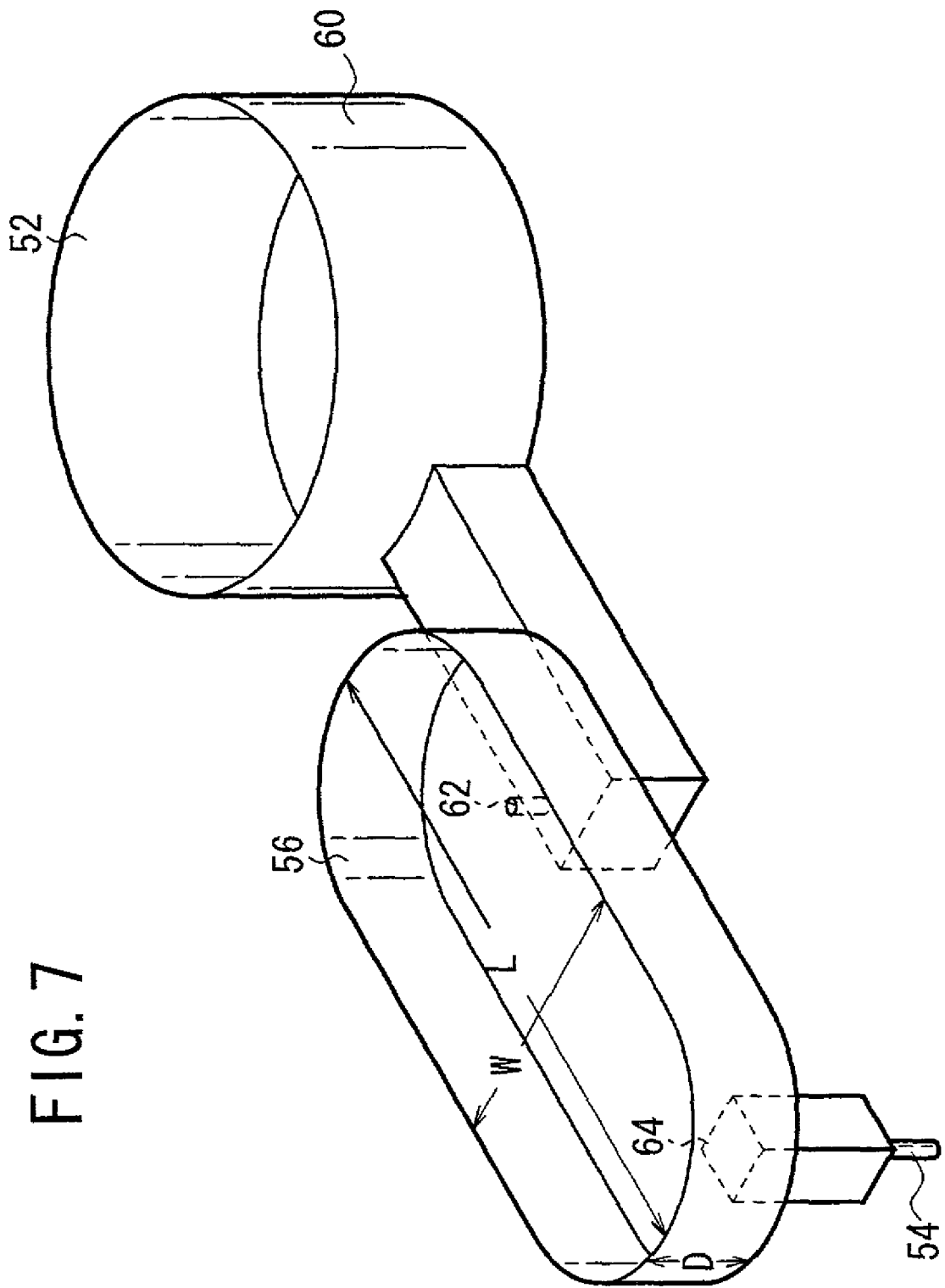
FIG. 7 is a perspective view illustrating the shape of a flow passage including a cavity formed in a substrate of the micropipette.

That is, the dimension of the cavity 56 differs depending on the type of the sample 14, the size of liquid droplets to be dropped, and the density of droplets. However, for example, when DNA fragments having 1 bp to 10,000 bp are dispersed in a X1 buffer solution (TE buffer) at a concentration of 0.3 µg/µ liter to obtain a sample 14 which is supplied at a pitch of several hundreds µm to give a liquid droplet diameter of hundred and several tens µmΦ, then it is preferable that the cavity length (L) is 1 to 5 mm, the cavity width (W) is 0.1 to 1 mm, and the cavity depth (D) is 0.1 to 0.5 mm as shown in FIG. 7. It is preferable that the inner wall of the cavity 56 is smooth without involving any projection to disturb the flow. It is preferable that the material of the cavity 56 is made of ceramics which has good affinity with respect to the sample 14.

When the shape as described above is adopted, the cavity 56 can be used as a part of the flow passage ranging from the sample-pouring port 52 to the sample discharge port 54. The sample 14 or the immobilization-reinforcing solution 16 can be introduced to the sample discharge port 54 without disturbing the flow of the sample 14 or the immobilization-reinforcing solution 16 which is moved from the sample-pouring port 52 via the introducing bore 60 and the first communication hole 62 to the inside of the cavity 56.

As shown in FIG. 5A, a plurality of pins 38 for positioning and fixing the micropipettes 34 are provided on the upper surface of the fixation plate 32. When the micropipette 34 is fixed on the fixation plate 32, the micropipette 34 is placed on the fixation plate 32 while inserting the pins 38 of the fixation plate 32 into positioning holes 90 (see FIG. 5C) provided at both sides of the substrate 50 of the micropipette 34. Thus, a plurality of micropipettes 34 are automatically positioned and aligned with a predetermined array arrangement.

Each of the fixing jigs 36 has a holder plate 100 for pressing the plurality of micropipettes 34 against the fixation plate 32. Insertion holes for inserting screws 102 thereinto are formed through both end portions of the holder plate 100 respectively. When the screws 102 are inserted into the insertion holes, and they are screwed into the fixation plate 32, then the plurality of micropipettes 34 can be pressed against the fixation plate 32 with the aid of the holder plate 100. One unit is constructed by the plurality of micropipettes 34, which are pressed by one holder plate 100. As shown in FIG. 5A, one unit is constructed by the five micropipettes 34 which are arranged in the direction of the column.

The holder plate 100 is formed with introducing holes 104 (see FIG. 5B) which are used to supply the samples 14 and the immobilization-reinforcing solutions 16 to the portions corresponding to the sample-pouring ports 52 of the respective micropipettes 34 when the plurality of micropipettes 34 are pressed. Tubes 106 for introducing the samples 14 and the immobilization-reinforcing solutions 16 to the introducing holes 104 are held at upper end portions of their respective introducing holes 104.

Considering the realization of the efficient wiring operation, it is preferable that the width of the holder plate 100 resides in such a dimension that the pads 76, 78 connected to their respective electrodes 70, 74 of the actuator section 58 are faced upwardly when the plurality of micropipettes 34 are pressed against the fixation plate 32.

As described above, the dispenser 30 is constructed such that the plurality of micropipettes 34, each having the sample-pouring port 52 and the sample discharge port 54 are provided in an upstanding manner with their respective sample discharge ports 54 directed downwardly.

That is, the micropipettes 34 are aligned and arranged such that their respective sample-pouring ports 52 are disposed on the upper side, the sample discharge ports 54 are disposed on the lower side, and their respective sample discharge ports 54 are aligned two-dimensionally. The samples 14 and the immobilization-reinforcing solutions 16 of mutually different types are discharged from the sample discharge ports 54 respectively.

In FIG. 5A, the both ends of the holder plate 100 are fixed by being tightened to the fixation plate 20 by the aid of the screws 102. However, the holder plate 100 may be fixed in accordance with other methods based on the mechanical procedure by using, for example, screws and springs, as well as based on an adhesive or the like.

As described above, the substrate 50 of the micropipette 34 and the portion of the base 46 of the actuator section 58 are formed of ceramics, for which it is possible to use, for example, fully stabilized zirconia, partially stabilized zirconia, alumina, magnesia, and silicon nitride.

Among them, the fully stabilized/partially stabilized zirconia is adopted most preferably, because the mechanical strength is large even in the case of the thin plate, the toughness is high, and the reactivity with the piezoelectric layer 72 and the electrode material is small.

When the fully stabilized/partially stabilized zirconia is used as the material, for example, for the portion of the base 46 of the actuator section 58, it is preferable that at least the portion (vibrating section 66), on which the piezoelectric layer 72 is formed, contains an additive such as alumina and titania.

Those piezoelectric ceramics usable for the piezoelectric layer 72 of the actuator section 58 include, for example, lead zirconate, lead titanate, lead magnesium niobate, lead magnesium tantalate, lead nickel niobate, lead zinc niobate, lead manganese niobate, lead antimony stannate, lead manganese tungstate, lead cobalt niobate, and barium titanate, as well as composite ceramics containing components obtained by combining any of them. However, in the embodiment of the present invention, a material containing a major component composed of lead zirconate, lead titinate, and lead magnesium niobate is preferably used, for the following reason.

That is, such a material has a high electromechanical coupling constant and a high piezoelectric constant. Additionally, such a material has small reactivity with the substrate material during the sintering of the piezoelectric layer 72, making it possible to stably form the product having a predetermined composition.

Further, in the embodiment of the present invention, it is also preferable to use ceramics obtained by appropriately adding, to the piezoelectric ceramics described above, for example, oxides of lanthanum, calcium, strontium, molybdenum, tungsten, barium, niobium, zinc, nickel, manganese, cerium, cadmium, chromium, cobalt, antimony, iron, yttrium, tantalum, lithium, bismuth, and stannum, or a combination of any of them, or compounds thereof.

For example, it is also preferable to use ceramics containing a major component composed of lead zirconate, lead titanate, and lead magnesium niobate, and further containing lanthanum and/or strontium.

On the other hand, it is preferable that the upper electrode 74 and the lower electrode 70 of the actuator section 58 are made of metal which is solid at room temperature and which is electrically conductive. For example, it is possible to use metal simple substance of, for example, aluminum, titanium, chromium, iron, cobalt, nickel, copper, zinc, niobium, molybdenum, ruthenium, palladium, rhodium, silver, stannum, tantalum, tungsten, iridium, platinum, gold, and lead, or alloy obtained by combining any of them. Further, it is also preferable to use a cermet material obtained by dispersing, in the metal described above, the same material as that of the piezoelectric layer 72 or the portion of the base 46.

In general, it is preferable that the nozzle sheet 48 is composed of a material suitable for the formation of the discharge port. It is desirable that the nozzle sheet 48 is composed of a resin including, for example, PET, polyimide, polyamide, maleimide, and polysulfone. In order to stably discharge the droplets, it is preferable that the portion, at which the solution is discharged, is subjected to a liquid-repelling treatment with fluororesin or silicon. In the embodiment of the present invention, a silicon-coated PET film, which is excellent in excimer laser machining performance and which is excellent in productivity, can be preferably adopted.

Further, it is also preferable to use a nozzle sheet composed of a metal sheet such as SUS which is excellent, for example, in drawing machining and punching out based on the use of a die. Also in this case, in order to stably discharge the droplets, it is preferable that the portion, at which the solution is discharged, is subjected to a liquid-repelling treatment with fluororesin or silicon.

Next, explanation will be made in detail below with reference to FIG. 8 for an exemplary method for supplying the sample onto the base plate 10 by using the dispenser 30.

Figure 8:
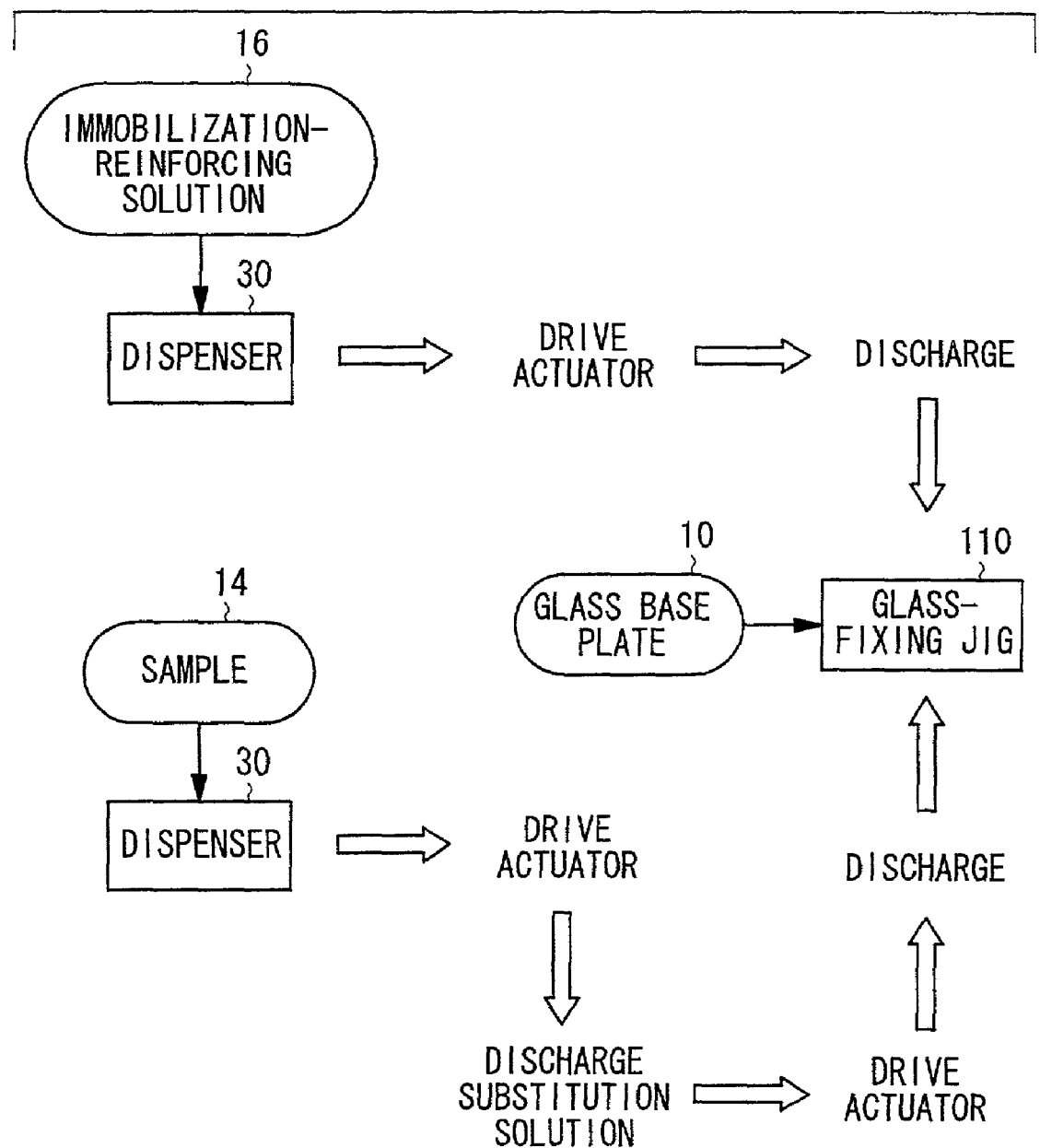
FIG. 8 illustrates an example of the method for producing the biochip by using the dispenser.

As shown in FIG. 8, a plurality of slide glass base plate 10, for example, twenty glass base plates 10, the surface of each of which is coated with the poly-L-lysine layer 12, are fixed on a glass-fixing jig 110. Subsequently, the immobilization-reinforcing solution 16 is charged into the cavity 56 of each of the micropipettes 34 via the introducing bore 104 of the fixing jig 36 from each of the tubes (not shown) of the dispenser 30 attached to the robot so that the dispenser 30 is freely movable over the glass base plate 10 while controlling the relative position with respect to the glass-fixing jig 110. The actuator section 58 is driven to discharge and supply the immobilization-reinforcing solution 16 onto the base plate 10 as shown in FIG. 4A.

In this procedure, the immobilization-reinforcing solution 16 may be supplied by using all of the ten micropipettes 34 shown in FIG. 5A. However, the priority is given to the stability of the shape of the supply area, and the supply is performed for the all by using one micropipette 34.

Subsequently, another disperser 30 is prepared, in which the interior of the micropipette 34 is previously filled with a substitution solution such as degassed pure water. The sample 14 is poured from the sample-pouring port 52, and then the actuator section 58 is driven to discharge the substitution solution. The interior of the cavity 56 is substituted with the sample 14 from the sample-pouring port 52.

At the stage at which the substitution is completed, the actuator section 58 is driven. As shown in FIG. 4B, the sample 14 is discharged and supplied onto the immobilization-reinforcing solution 16 having been supplied onto the base plate 10 set on the same glass-fixing jig. Accordingly, as shown in FIG. 4C, the biochip 20 is produced, in which the sample 14 containing the immobilization-reinforcing solution 16 is supplied onto the base plate 10.

Next, explanation will be made below with reference to FIGS. 9A to 11C for other illustrative embodiments of the method for producing biochip according to the present invention.

Figure 9A:
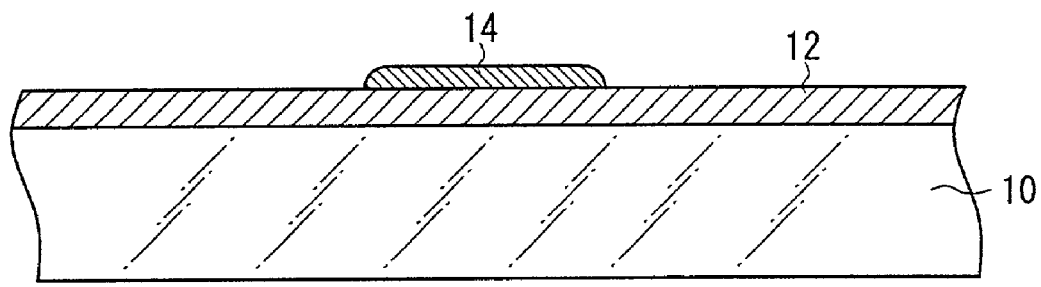
FIG. 9A shows a step illustrating a state in which a sample is supplied onto a base plate.
Figure 9B:
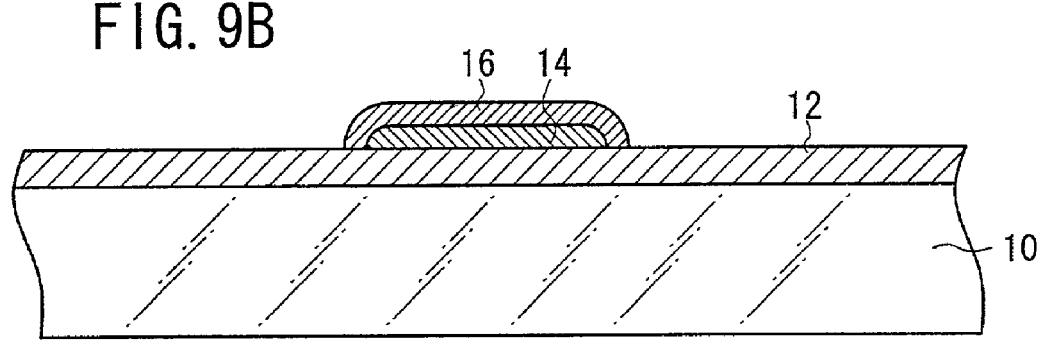
FIG. 9B shows a step illustrating a state in which an immobilization-reinforcing solution is supplied onto the sample on the base plate.
Figure 9C:
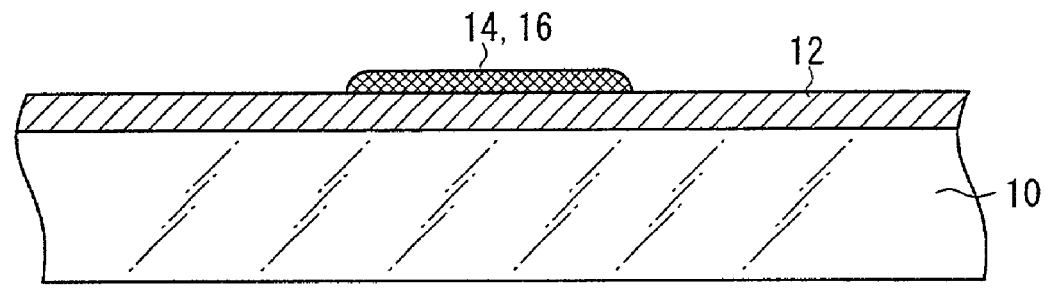
FIG. 9C shows a step illustrating a state in which the sample and the immobilization-reinforcing solution are integrated into one unit.

As shown in FIGS. 9A to 9C, a method for producing a biochip according to a second embodiment is approximately the same as the method for producing the biochip according to the first embodiment described above in that the sample 14, the base plate 10, and the dispenser 30 are used in the same manner. However, the former is different from the latter in that the order of supply of solutions onto the base plate 10 is inverted for the immobilization-reinforcing solution 16 and the sample 14.

That is, at first, as shown in FIG. 9A, the sample 14 is firstly supplied. After that, as shown in FIG. 9B, the immobilization-reinforcing solution 16 is supplied in a superimposed manner onto the area to which the sample 14 has been supplied, followed by being integrated into one unit as shown in FIG. 9C.

In the second embodiment, the immobilization-reinforcing solution 16 is required to have such a physical property that the immobilization-reinforcing solution 16 should diffuse in the sample 14 to arrive at the base plate 10. Therefore, it is possible to preferably adopt a monomer or a polymer having a relatively low degree of polymerization.

Figure 10A:
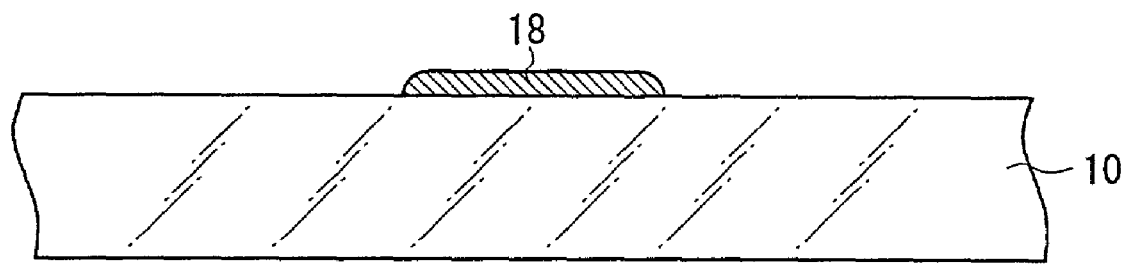
FIG. 10A shows a step illustrating a state in which an immobilization solution is supplied onto a base plate.
Figure 10B:
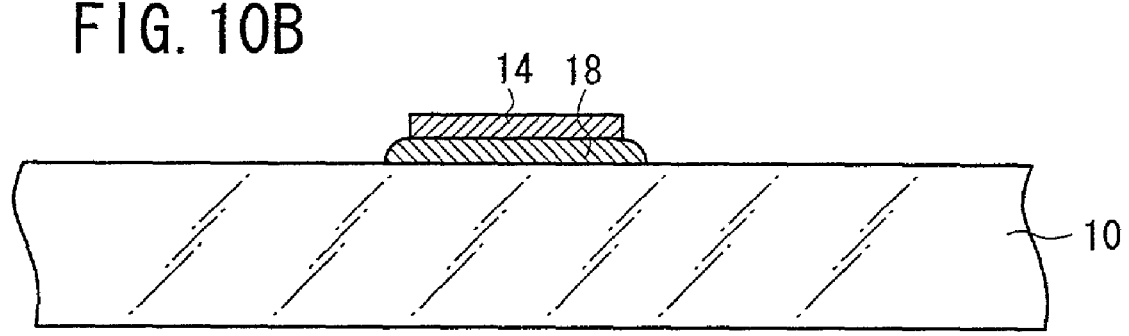
FIG. 10B shows a step illustrating a state in which a sample is supplied onto the immobilization solution on the base plate.

Next, as shown in FIGS. 10A and 10B, a method for producing a biochip according to a third embodiment is approximately the same as the method for producing the biochip according to the first embodiment described above in that the sample 14, the base plate 10, and the dispenser 30 are used in the same manner. However, the former is different from the latter in that the immobilization solution 18 is supplied onto the base plate 10, and then the sample 14 is supplied to the area of the immobilization solution 18.

That is, at first, as shown in FIG. 10A, the immobilization solution 18 is firstly supplied onto the base plate 10. After that, as shown in FIG. 10B, the sample 14 is supplied in a superimposed manner onto the area to which the immobilization solution 18 has been supplied.

In the third embodiment, even when the sample 14 is supplied to those other than the area to which the immobilization solution 18 has been supplied, the sample 14 is not immobilized on the base plate 10. A poly-L-lysine solution, which is prepared by adding poly-L-lysine to distilled water, is adopted as the immobilization solution 18.

Figure 11A:
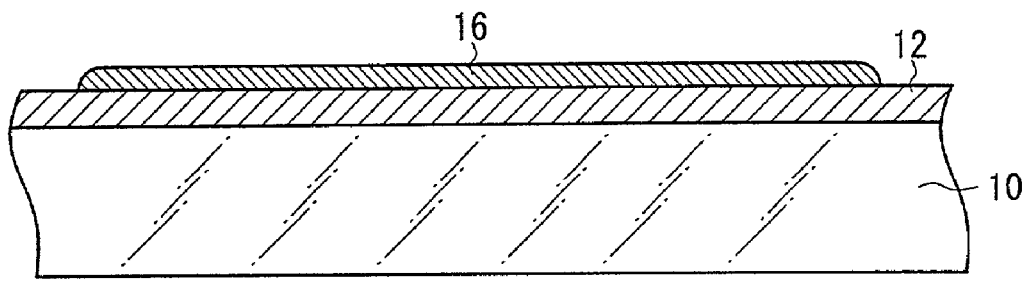
FIG. 11A shows a step illustrating a state in which an immobilization-reinforcing solution is supplied onto a base plate.
Figure 11B:
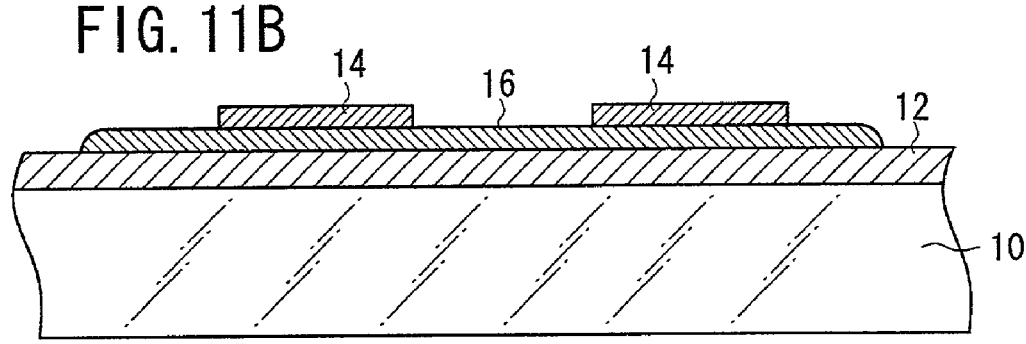
FIG. 11B shows a step illustrating a state in which a sample is supplied onto the immobilization-reinforcing solution on the base plate.
Figure 11C:
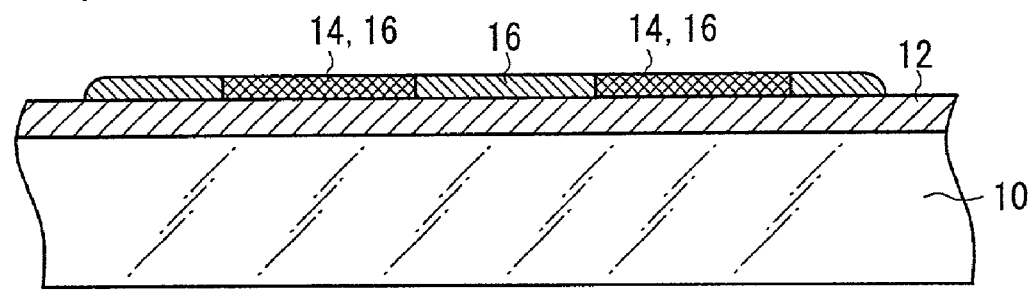
FIG. 11C shows a step illustrating a state in which the sample and the immobilization-reinforcing solution are integrated into one unit.

Next, as shown in FIGS. 11A to 11C, a method for producing a biochip according to a fourth embodiment differs in that the immobilization-reinforcing solution 16 is supplied onto the base plate 10 over an area which includes two or more areas to each of which the sample 14 is to be supplied, and then the sample 14 is supplied thereonto.

That is, at first, as shown in FIG. 11A, the immobilization-reinforcing solution 16 is formed by means of the screen printing method on a substantially entire surface of the base plate 10. Subsequently, as shown in FIG. 11B, the sample 14 is supplied in accordance with the ink-jet method in the same manner as in the embodiments described above. After that, as shown in FIG. 11C, the immobilization-reinforcing solution 16 and the sample 14 are integrated into one unit to be strongly immobilized on the base plate 10 in the vicinity of the area to which the sample 14 has been supplied.

As described above, in the methods for producing the biochips according to the first to fourth embodiments, the sample 14 containing DNA fragments and the immobilization-reinforcing solution 16 or the immobilization solution 18 for reliably immobilizing the sample 14 are supplied separately from each other to produce the biochip 20. Accordingly, the immobilization is reliably achieved, and the phenomenon, in which minute spots are peeled off, is extremely decreased.

Further, it is unnecessary to provide the step of mixing the sample 14 and the immobilization-reinforcing solution 16 or the immobilization solution 18. Further, it is enough to use a slight amount of the immobilization-reinforcing solution 16 or the immobilization solution 18 required to immobilize the minute amount of the sample 14 supplied onto the base plate 10. Therefore, it is possible to greatly decrease the amount of the immobilization-reinforcing solution 16 or the immobilization solution 18, which is advantageous to simplify the production steps and reduce the cost.

Further, it is unnecessary that the sample discharge port 54 of the dispenser 30 for supplying the immobilization-reinforcing solution 16 or the immobilization solution 18 is conformed to the supply specification for the sample 14. The sample discharge port 54 can be designed exclusively for the immobilization-reinforcing solution 16 or the immobilization solution 18 (for example, to have a structure to scarcely suffer from drying). Thus, it is possible to improve the degree of freedom of the design.

Further, the sample 14 is not solidified during the supply. Therefore, the sample 14 and the immobilization-reinforcing solution 16 or the immobilization solution 18 can be supplied with enough time margin. Accordingly, the sample 14 and the immobilization-reinforcing solution 16 or the immobilization solution 18 can be supplied while considering, for example, the positioning of the supply portion, the supply timing depending on the type of the sample 14, and the supply amount. It is possible to improve the quality of the biochip 20 and improve the yield.

Figure 12:
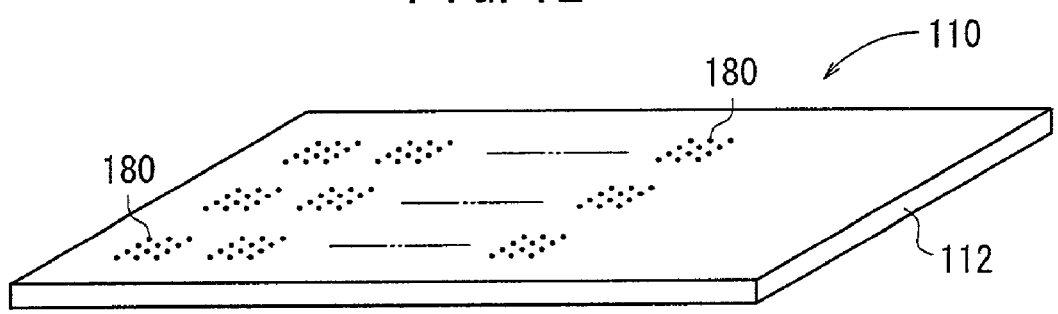
FIG. 12 is a perspective view illustrating a biochip according to a fifth embodiment.

Next, as shown in FIG. 12, a biochip 110 according to a fifth embodiment comprises a large number of spots 180 based on samples containing captures, the spots 180 being arranged on a base plate 112 by supplying, onto the base plate 112, a plurality of types of the samples containing captures to be used to specifically react with a specimen in order to obtain information on a structure or a function of the specimen.

Figure 13:
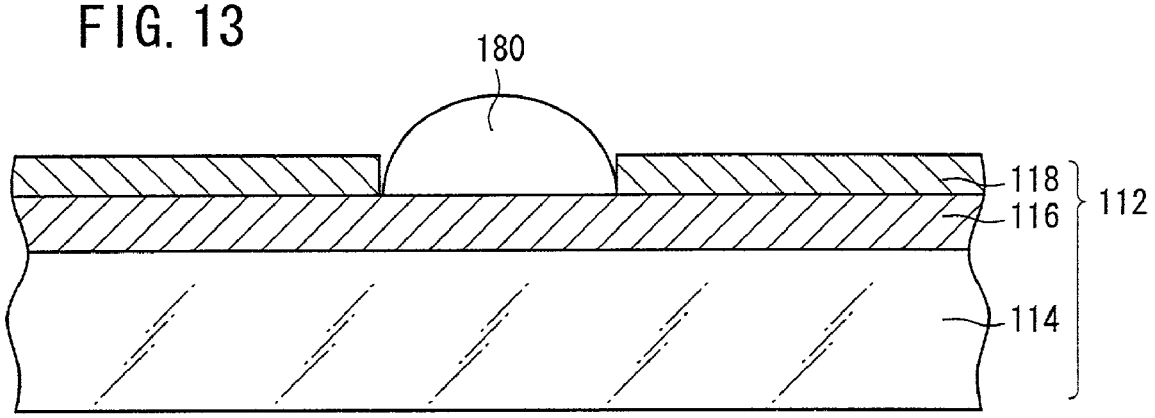
FIG. 13 is a magnified sectional view illustrating the biochip according to the fifth embodiment.

As shown in FIG. 13, the base plate 112 comprises a main base plate body 114 which is composed of, for example, a microscopic slide glass, a first substance 116 which is formed on the upper surface of the main base plate body 114 and which acts on the immobilization of the capture onto the base plate 112, and a second substance 118 which is formed at parts other than portions at which the spots 180 are to be formed on the first substance 116 and which inhibits at least the immobilization of the capture onto the base plate 112.

Especially, the second substance 118 is composed of a substance which inhibits the immobilization of the capture onto the base plate 112 and which inhibits the contact of the specimen with the base plate 112.

In this case, the capture includes, for example, nucleic acids and proteins. The nucleic acid includes DNA and/or fragment thereof or amplified product thereof; cDNA and/or fragment thereof or amplified product thereof; RNA or antisense RNA and/or fragment thereof or amplified product thereof; chemically synthesized DNA or amplified product thereof; and chemically synthesized RNA or amplified product thereof.

On the other hand, the protein includes, for example, antigen, antibody, lectin, adhesin, receptor for physiologically active substance, and peptide.

Next, the first substance 116 and the second substance 118 will be explained. At first, when the first substance 116 is a chemical substance having positive charge to act on the immobilization of the captures on the base plate by means of ionic bond, the second substance 118 is a chemical substance having negative charge.

In this case, the first substance 116 is a silane coupling agent such as γ-γ-aminopropyltriethoxysilane, poly-L-lysine, polyethyleneimine, or polyalkylamine, and the second substance 118 is succinic acid or polyacrylic acid.

When the first substance 116 is a chemical substance having an active group for modifying the surface of the base plate 112 to act on the immobilization of the captures onto the base plate 112 by means of covalent bond by effecting a chemical reaction of the active group introduced into the surface of the base plate 112 and a functional group introduced by modifying the captures, the second substance 118 is a chemical substance having the functional group reactive with the active group.

In this case, the chemical reaction to achieve the covalent bond is a reaction of amino group and aldehyde group, a reaction of amino group and N-hydroxysuccinimido group, a reaction of amino group and carboxyl group, a reaction of amino group and epoxy group, or a reaction of thiol group and epoxy group.

In such a case, the first substance 116 is a mixture of γ-aminopropyltriethoxysilane and glutaraldehyde, a mixture of γ-aminopropyltriethoxysilane, succinic anhydride, and N-hydroxysuccinimido, a mixture of γ-aminopropyltriethoxysilane and succinic anhydride, epichlorohydrin, or bisoxysilane, and the second substance 118 is glycine as amino acid, tris having amino group, ethanolamine, cysteine having thiol group, glutathione, or thioglycol.

When the first substance 116 is a chemical substance for modifying the surface of the base plate 112 to act on the immobilization of the captures onto the base plate 112 by means of affinity bond, the second substance 118 is a substance which makes the affinity bond with the same chemical substance as the capture.

In this case, the first substance 116 is avidin, streptavidin, protamine, histone, biotin, antigen, antibody combining protein, or antibody, and the second substance 118 is avidin, streptavidin, biotin, nucleic acid, antigen, antibody combining protein, or antibody.

When the first substance 116 is a chemical substance including hydrophobic group such as styrene group, phenyl group, and alkyl group for modifying the surface of the base plate 112 to act on the immobilization of the captures onto the base plate 112 by means of hydrophobic bond, the second substance 118 is an amphiphilic substance.

In this case, the first substance 116 is polystyrene or alkylbenzene, and the second substance 118 is gelatin or casein.

Alternatively, the second substance 118 is a resin containing silicon or fluorine for all of the first substances 116 referred to above. The resin containing silicon or fluorine has liquid repellency with respect to the aqueous solution. Therefore, an effect is also obtained such that the sample solution itself is repelled during the use of the biochip, in addition to the fact that the resin containing silicon or fluorine effectively prevents the first substance from contact with the base plate to avoid immobilization thereof. The background noise with respect to the spot signal has been reduced to be not more than ½.

Next, explanation will be made with reference to FIGS. 14 to 16C for a method for producing the biochip 110 according to the fifth embodiment.

Figure 14A:
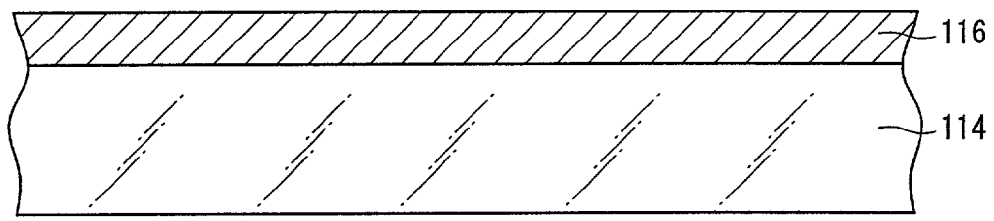
FIG. 14A shows a progress step illustrating a state in which a first substance is formed on an upper surface of a main base plate body.

At first, as shown in FIG. 14A, the first substance 116 is formed on the entire surface of the main base plate body 114 by means of, for example, the screen printing method. Of course, it is also allowable to use, as the main base plate body 114, one in which the first substance 116 is previously formed on the upper surface.

Figure 14B:
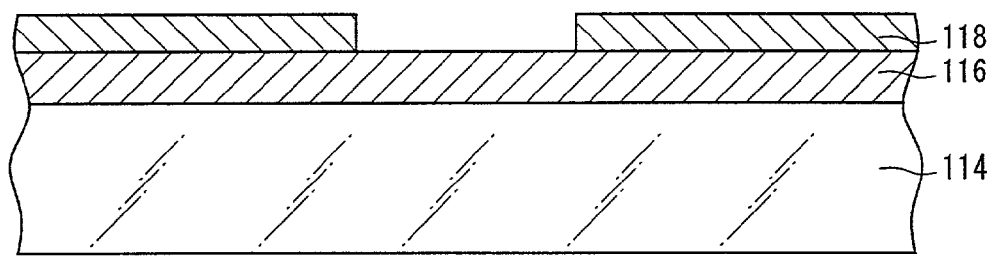
FIG. 14B shows a progress step illustrating a state in which a second substance is formed at parts other than portions at which spots are to be formed on the first substance.

Subsequently, as shown in FIG. 14B, the second substance 118 is supplied by means of the ink-jet system to parts other than the portions at which the spots 180 are to be formed on the first substance 116 formed on the main base plate body 114.

The second substance 118 can be supplied by the ink-jet system by using the dispenser 30 as shown in FIG. 5A in the same manner as in the embodiment described above.

Especially, as described later on, the dispenser 30 is also used when the sample containing the capture is supplied onto the base plate 12. In this case, the cavities 56 of the respective micropipettes 34 are filled with the samples containing the captures. The samples in the cavities are discharged at the predetermined speed from the sample discharge ports 54 communicating with the cavities 56, in accordance with the decrease in volumes of the cavities 56. The samples discharged from the micropipettes 34 are supplied onto the base plate 112 as shown in FIG. 12. Thus, the biochip 110, in which the samples are aligned and immobilized as the spots 180, is produced.

The cavity (pressurizing chamber) 56 of each of the micropipettes 34 is formed to have such a flow passage dimension that the sample or the second substance 118 described above is moved therethrough. The cavity 56 is preferably made of a material of ceramics having good affinity with respect to the second substance 118 and the sample.

Next, explanation will be made in detail below with reference to FIG. 15 for an exemplary method for supplying the second substance 118 and the sample onto the main base plate body 114 by using the dispenser 30.

Figure 15:
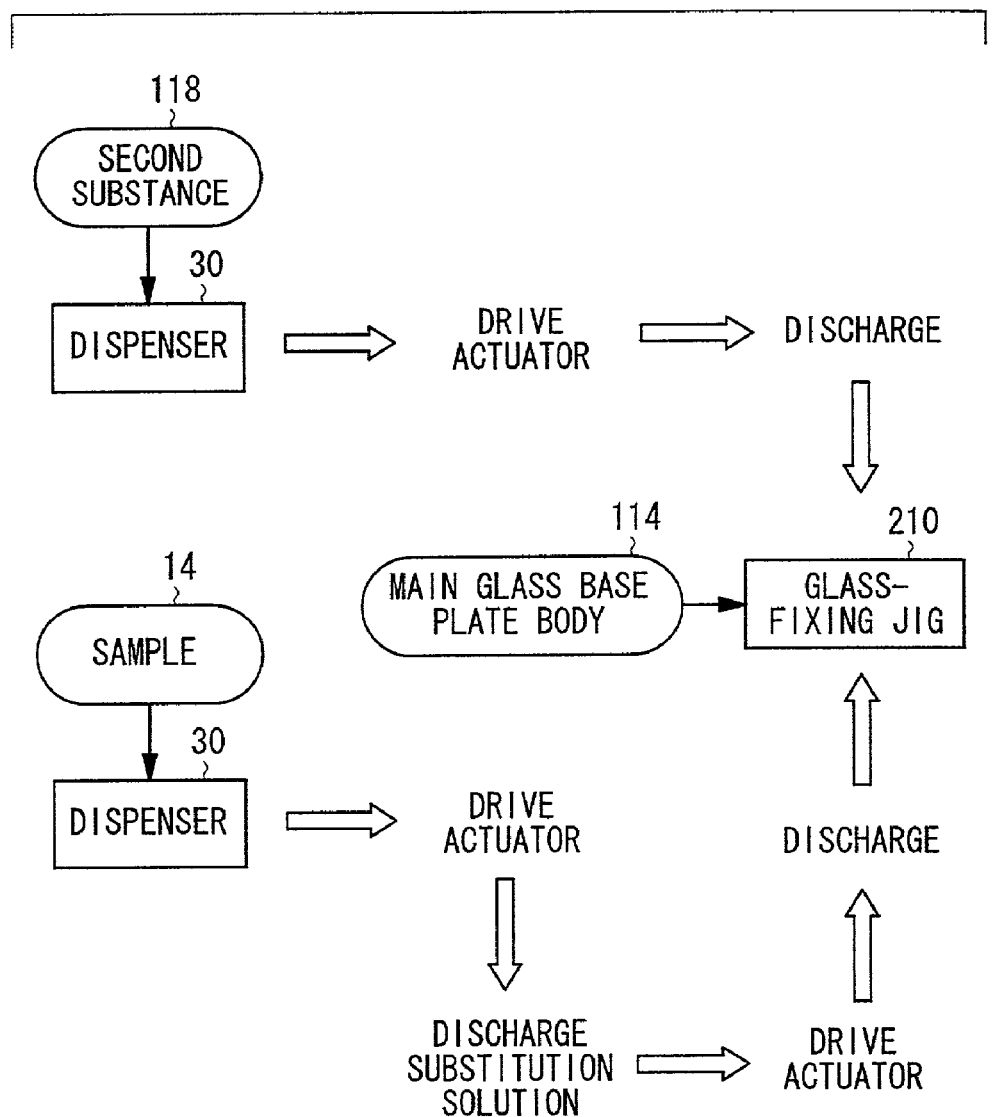
FIG. 15 shows an example of the method for producing the biochip by using the dispenser.

As shown in FIG. 15, a plurality of main glass base plate bodies 114, for example, twenty main glass base plate bodies 114, the surface of each of which is formed with the first substance 116, are fixed on a glass-fixing jig 210. Subsequently, the second substance 118 is charged into the cavity 56 of each of the micropipettes 34 via the introducing bore 104 of the fixing jig 36 from each of the tubes (not shown) of the dispenser 30 attached to the robot so that the dispenser 30 is freely movable over the main glass base plate body 114 while controlling the relative position with respect to the glass-fixing jig 210. The actuator section 58 is driven to discharge and supply the second substance 118 onto the parts other than the portions at which the spots 180 are to be formed on the first substance formed on the main base plate body as shown in FIG. 14B.

In this procedure, the second substance 118 may be supplied by using all of the ten micropipettes 34 shown in FIG. 5A. However, the priority is given to the stability of the shape of the supply area, and the supply is performed for the all by using one micropipette 34.

Subsequently, another disperser 30 is prepared, in which the interior of the micropipette 34 is previously filled with a substitution solution such as degassed pure water. The sample 14 containing the capture is poured from the sample-pouring port 52, and then the actuator section 58 is driven to discharge the substitution solution. The interior of the cavity 56 is substituted with the sample 14 from the sample-pouring port 52.

At the stage at which the substitution is completed, the actuator section 58 is driven. As shown in FIG. 13, the sample 14 is discharged and supplied to the part at which the spot 180 is to be formed, i.e., to the part at which the first substance 116 is exposed, on the main base plate body 114 set on the same glass-fixing jig 210. Accordingly, as shown in FIG. 12, the biochip 110 is produced, in which the large number of spots 180 based on the samples 14 are arranged on the base plate 112.

As described above, in the biochip 110 and the method for producing the same according to the fifth embodiment, the first substance 116, which acts on the immobilization of the capture onto the base plate 112, is formed on the entire surface of the main base plate body 114. The second substance 112, which inhibits the immobilization of the capture onto the base plate 112 and which inhibits the contact of the specimen with the base plate 112, is formed at the parts other than the portions at which the spots 180 are to be formed on the first substance 116 having been formed on the main base plate body 114. Therefore, the shape and the arrangement form of the spots 180 are determined by the shape of the parts at which the second substance 118 is not formed.

Accordingly, for example, inconveniences, in which the arrangement spacing between the spots 180 is dispersed and the spots 180 are placed close to one another, disappear when the samples are supplied onto the base plate 112. Further, when the sample cannot be supplied to the prescribed position, the sample is prevented from contact with the base plate 112 owing to the presence of the second substance 118. Therefore, no contamination source is generated.

Further, splashes or mists, which are caused by the satellite phenomenon often caused during the discharge of the sample when the sample is supplied in accordance with the ink-jet system, are prevented from contact with the base plate 112 owing to the presence of the second substance 118. Therefore, it is possible to eliminate the problem of satellites having been caused by the ink-jet system.

That is, in the fifth embodiment, it is possible to inexpensively obtain the high quality biochip 110. It is possible to simplify the production steps, reduce the cost, and improve the yield of the biochip 110.

The fifth embodiment described above is illustrative of a case in which the second substance 118 is supplied in accordance with the ink-jet system by using the dispenser 30. Alternatively, the second substance 118 may be formed in accordance with the screen printing method. In this case, it is possible to shorten the time required to supply the second substance 118 to the parts other than the portions at which the spots 180 are to be formed. It is possible to improve the throughput and reduce the number of steps.

Figure 16A:
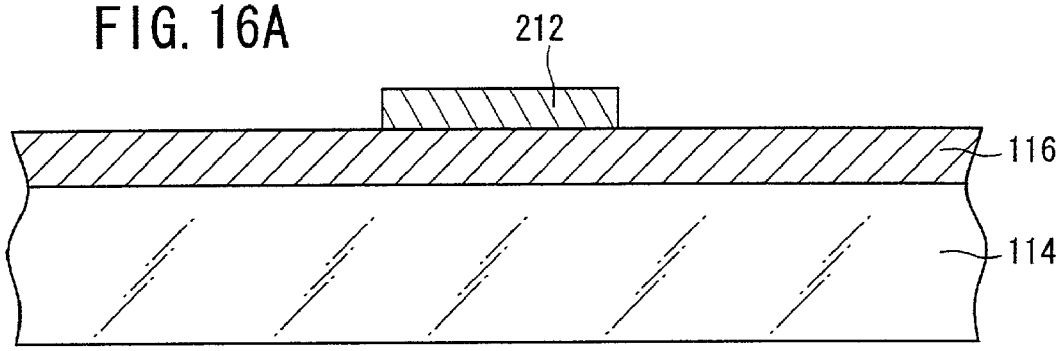
FIG. 16A shows a progress step illustrating a state in which a resist is formed at a part at which a spot is to be formed on a first substance formed on the main base plate body.
Figure 16B:
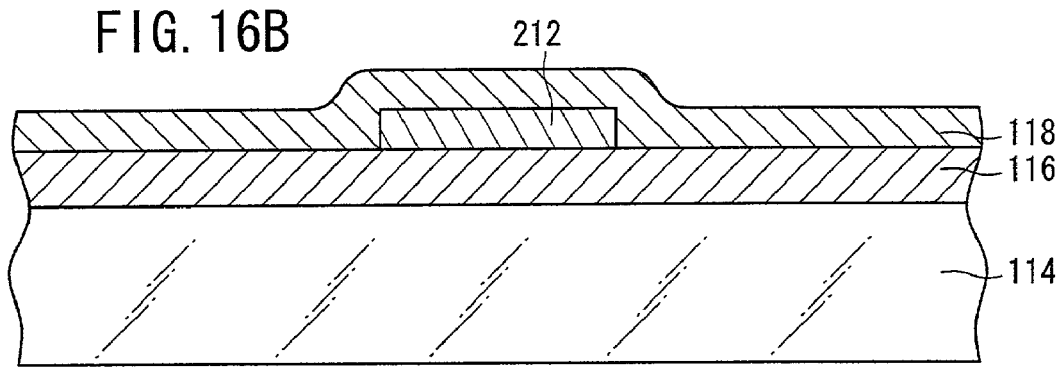
FIG. 16B shows a progress step illustrating a state in which a second substance is formed on an entire surface including the resist.
Figure 16C:
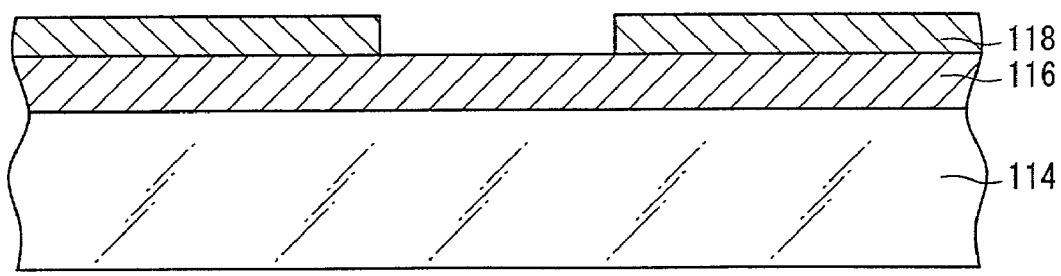
FIG. 16C shows a progress step illustrating a state in which the resist is subjected to lift-off.

As another alternative method, the second substance 118 may be formed in accordance with the dipping method. In this case, for example, as shown in FIG. 16A, a resist 212 is formed at portions at which the spots 180 are to be formed on the first substance 116 having been formed on the main base plate body 114. After that, as shown in FIG. 16B, the second substance 118 is formed in accordance with the dipping method over the entire surface including the resist 212. After that, as shown in FIG. 16C, the resist 212 is subjected to lift-off. Accordingly, the second substance 118 is formed at the parts other than the portions at which the spots 180 are to be formed.

The method based on the dipping is preferred when the second substance 118 has a low viscosity. Also in this case, it is possible to shorten the time required to supply the second substance 118 to the parts other than the portions at which the spots 180 are to be formed. It is possible to improve the throughput and reduce the number of steps.

It is a matter of course that the biochip and the method for producing the same according to the present invention are not limited to the embodiments described above, which may be embodied in other various forms without deviating from the gist or essential characteristics of the present invention.

What is claimed is:

1. A method for producing a biochip comprising the steps of:

providing a substantially planar base plate;

supplying, onto the upper surface of said base plate, a plurality of solution samples, each containing a capture used to specifically react with a specimen in order to obtain information on a structure or a function of said specimen; and supplying a solution containing no capture in accordance with an ink-jet system separately from and in the same location as each of said solution samples, wherein one of said solution sample and said solution containing no capture is supplied onto the other one of said solution sample and said solution containing no capture while said other one of said solution sample and said solution containing no capture is in liquid form, has a top portion, and has a circumferential portion, said top portion being positioned higher with respect to said base late than said circumferential portion.

2. The method for producing said biochip according to claim 1, wherein said solution sample is supplied in accordance with an ink-jet system.

3. The method for producing said biochip according to claim 1, wherein said solution containing no capture is an immobilization solution for immobilizing said captures onto said base plate, or an immobilization-reinforcing solution for reinforcing immobilization of said captures onto said base plate.

4. The method for producing said biochip according to claim 3, further comprising preparing a jig to which a plurality of said base plates are set, wherein said solution sample and said solution containing no capture are supplied in a state in which said base plates are fixed on said jig.

5. The method for producing said biochip according to claim 3, wherein an area, in which said solution containing no capture is supplied onto said base plate, is substantially the same as an area to which said solution sample is supplied, or an area which includes said area to which said solution sample is supplied, said area having a substantially circular shape.

6. The method for producing said biochip according to claim 3, wherein an area, in which said solution containing no capture is supplied onto said base plate, has a size which includes two or more areas to each of which said solution sample is supplied.

7. The method for producing said biochip according to claim 3, wherein said immobilization solution or said immobilization-reinforcing solution is a solution with which immobilization or immobilization reinforcement is advanced by mixing said immobilization solution or said immobilization-reinforcing solution with said solution sample.

8. The method for producing said biochip according to claim 3, wherein said solution sample is supplied onto said base plate, and then said immobilization solution or said immobilization-reinforcing solution is supplied to parts to which said solution sample has been supplied.

9. The method for producing said biochip according to claim 3, wherein said immobilization solution or said immobilization-reinforcing solution is supplied onto said base plate, and then said solution sample is supplied to parts to which said immobilization solution or said immobilization-reinforcing solution has been supplied.

10. The method for producing said biochip according to claim 9, wherein said immobilization solution is a solution of chemical substance having positive charge, and said capture is immobilized by means of ionic bond.

11. The method for producing said biochip according to claim 10, wherein said chemical substance is γ-aminopropyltriethoxysilane.

12. The method for producing said biochip according to claim 10, wherein said chemical substance is poly-L-lysine, polyalkylamine or a silane coupling agent.

13. The method for producing said biochip according to claim 9, wherein said immobilization solution includes a chemical substance for chemically modifying a base plate surface, and a functional group introduced into said base plate surface and a functional group introduced by modifying said capture are subjected to a chemical reaction to immobilize said capture onto said base plate by means of covalent bond.

14. The method for producing said biochip according to claim 13, wherein said chemical reaction is a reaction of amino group and aldehyde group, a reaction of amino group and N-hydroxysuccinimido group, a reaction of amino group and carboxyl group, a reaction of amino group and epoxy group, or a reaction of thiol group and epoxy group.

15. The method for producing said biochip according to claim 9, wherein said immobilization solution includes avidin, streptavidin, protamine, or histone.

16. The method for producing said biochip according to claim 9, wherein said immobilization solution is a solution containing a hydrophobic group.

17. The method for producing said biochip according to claim 9, wherein said immobilization-reinforcing solution includes a water-retentive substance.

18. The method for producing said biochip according to claim 17, wherein said water-retentive substance is colominic acid, hyaluronic acid, or mixture of colominic acid and hyaluronic acid.

19. The method for producing said biochip according to claim 9, wherein said immobilization-reinforcing solution includes a high-molecular substance.

20. The method for producing said biochip according to claim 19, wherein said high-molecular substance is one of an acidic polymer, a basic polymer, a neutral polymer, and a protein.

21. The method for producing said biochip according to claim 19, wherein said high-molecular substance is one of CM-cellulose, nitrocellulose, polyacrylic acid, and alginic acid.

22. The method for producing said biochip according to claim 19, wherein said high-molecular substance is one of polyethyleneimine and polyacrylamide.

23. The method for producing said biochip according to claim 19, wherein said high-molecular substance is one of methyl cellulose, polyethylene glycol, and polypropylene glycol.

24. The method for producing said biochip according to claim 19, wherein said high-molecular substance is one of BSA, egg albumin, and lysozyme.

25. The method for producing said biochip according to claim 9, wherein said immobilization solution is a solution containing one of a phenyl group and an alkyl group.

26. The method for producing said biochip according to claim 3, wherein said immobilization solution or said immobilization-reinforcing solution and said solution sample are supplied substantially simultaneously onto said base plate.

27. The method for producing said biochip according to claim 1, wherein said captures are nucleic acids.

28. The method for producing said biochip according to claim 27, wherein said nucleic acid is DNA and/or fragment thereof or amplified product thereof; cDNA and/or fragment thereof or amplified product thereof; RNA or antisense RNA and/or fragment thereof or amplified product thereof; chemically synthesized DNA or amplified product thereof; or chemically synthesized RNA or amplified product thereof.

29. The method for producing said biochip according to claim 1, wherein said captures are proteins.

30. The method for producing said biochip according to claim 29, wherein said protein is antigen, antibody, lectin, adhesin, receptor for physiologically active substance, or peptide.

31. The method for producing said biochip according to claim 1, wherein said solution containing no capture is of a common composition used with a plurality of different solution samples.

32. The method for producing said biochip according to claim 1, wherein said other one of said solution sample and said solution containing no capture is said solution containing no capture.

33. The method for producing said biochip according to claim 1, wherein said circumferential portion is exposed to atmosphere at a point in contact with said upper surface of said base plate.

34. The method for producing said biochip according to claim 1, wherein a supply area of said other one of said solution sample and said solution containing no capture is made wider than a supply area of said one of said solution sample and said solution containing no capture.

* * * * *